United States Patent
Telang et al.

(10) Patent No.: US 12,377,087 B2
(45) Date of Patent: *Aug. 5, 2025

(54) COMPOUNDS FOR THE TREATMENT OF CANCER

(71) Applicant: UNIVERSITY OF LOUISVILLE RESEARCH FOUNDATION, INC., Louisville, KY (US)

(72) Inventors: Sucheta Telang, Louisville, KY (US); Jason Chesney, Louisville, KY (US); John O. Trent, Louisville, KY (US)

(73) Assignee: UNIVERSITY OF LOUISVILLE RESEARCH FOUNDATION, INC., Louisville, KY (US)

( * ) Notice: Subject to any disclaimer, the term of this patent is extended or adjusted under 35 U.S.C. 154(b) by 997 days.

This patent is subject to a terminal disclaimer.

(21) Appl. No.: 17/097,080

(22) Filed: Nov. 13, 2020

(65) Prior Publication Data
US 2021/0145821 A1    May 20, 2021

Related U.S. Application Data

(62) Division of application No. 15/568,751, filed as application No. PCT/US2016/028868 on Apr. 22, 2016, now Pat. No. 10,881,654.

(60) Provisional application No. 62/152,239, filed on Apr. 24, 2015.

(51) Int. Cl.
| | |
|---|---|
| C07D 215/42 | (2006.01) |
| A61K 31/4545 | (2006.01) |
| A61K 31/47 | (2006.01) |
| A61K 31/4706 | (2006.01) |
| A61P 35/00 | (2006.01) |
| C07D 215/46 | (2006.01) |

(52) U.S. Cl.
CPC ...... *A61K 31/4706* (2013.01); *A61K 31/4545* (2013.01); *A61K 31/47* (2013.01); *A61P 35/00* (2018.01)

(58) Field of Classification Search
CPC .. C07D 215/38; C07D 215/42; C07D 215/46; A61K 31/4706; A61K 31/47; A61P 35/00
USPC .................................................. 546/159, 162
See application file for complete search history.

(56) References Cited

U.S. PATENT DOCUMENTS

| | | | | |
|---|---|---|---|---|
| 3,957,791 | A | * 5/1976 | Simpson | ............. C07D 215/46 |
| | | | | 546/159 |
| 4,035,367 | A | 7/1977 | Simpson | |
| 7,759,392 | B2 | 7/2010 | Soldato | |
| 8,088,385 | B2 | 1/2012 | Chesney et al. | |
| 8,283,332 | B2 | 10/2012 | Telang et al. | |
| 8,299,265 | B2 | * 10/2012 | Okuno | ................ C07D 211/62 |
| | | | | 548/161 |
| 10,774,046 | B2 | * 9/2020 | Telang | ................ C07D 215/42 |
| 10,881,654 | B2 | * 1/2021 | Telang | .................... A61P 35/00 |
| 2010/0267815 | A1 | 10/2010 | Telang et al. | |
| 2010/0273841 | A1 | 10/2010 | Okuno et al. | |
| 2013/0289083 | A1 | 10/2013 | Mautino et al. | |
| 2015/0376132 | A1 | * 12/2015 | Lee | ........................ A61P 21/00 |
| | | | | 546/163 |

FOREIGN PATENT DOCUMENTS

| | | |
|---|---|---|
| WO | 2014/134705 A1 | 9/2014 |
| WO | 2015/040169 A1 | 3/2015 |
| WO | 2016/172499 A1 | 10/2016 |

OTHER PUBLICATIONS

CAS RN 1328879-22-6 entered STN Sep. 6, 2011.*
CAS RN 1328552-48-2 entered STN Sep. 5, 2011.*
CAS RN 1328284-97-4 entered STN Sep. 5, 2011.*
Solomon et al. Bioorganic & Medicinal Chemistry 2005, 13, 2157-2165.*
Raj et al. Chem Biol Drug Des 2014, 83, 191-197.*
CAS RN 1705069-60-8, entered STN May 15, 2015.*
CAS RN 1705244-08-1, entered STN May 15, 2015.*
PCT/US2016/028868 ISR mailed Jul. 26, 2016, 3 pages.
PCT/US2016/028868 Written Opinion mailed Jul. 26, 2016, 9 pages.
Chenna et al., "Multiple sequence alignment with the Clustal series of programs" Nucleic Acids Res (2003) vol. 31, No. 13, pp. 3497-3500.
Chesney et al., "Fructose-2,6-bisphosphate synthesis by 6-phosphofructo-2-kinase/fructose-2,6-bisphosphatase 4 (PFKFB4) is required for the glycolytic response to hypoxia and tumor growth" Oncotarget (2014) vol. 5, No. 16, pp. 6670-6686.
Chesney et al., "Targeting the sugar metabolism of tumors with a first-in-class 6-phosphofructo-2-kinase (PFKFB4) Inhibitor" Oncotarget (2015) vol. 6, No. 20, pp. 18001-18011.
Colosia et al., "Isolation of a cDNA clone for rat liver 6-phosphofructo 2-kinase/fructose 2,6-bisphosphatase" Biochem Biophys Res Commun (1987) vol. 143, No. 3, pp. 1092-1098.
El-Maghrabi et al., "Tissue distribution, immunoreactivity, and physical properties of 6-phosphofructo-2-kinase/fructose-2,6-bisphosphatase" Proc Natl Acad Sci USA (1986) vol. 83, No. 14, pp. 5005-5009.
Finn et al., "The cyclin-dependent kinase 4/6 inhibitor palbociclib in combination with letrozole versus letrozole alone as first-line treatment of oestrogen receptor-positive, HER2-negative, advanced breast cancer (PALOMA-1/TRIO-18): a randomised phase 2 study" Lancet Oncol (2015) vol. 16, No. 1, pp. 25-35.
Ghosh et al., "Discovery of 4-(4-(2-((5-Hydroxy-1,2,3,4-tetrahydronaphthalen-2-yl)(propyl)amino)ethyl)piperazin-1-yl)quinolin-8-ol and Its Analogues as Highly Potent Dopamine D2/D3 Agonists and as Iron Chelator: In Vivo Activity Indicates Potential Application in Symptomatic and Neuroprotective Therapy for Parkinson's Disease" J. Med. Chem. (2010) vol. 53, pp. 2114-2125.
Goidts et al., "RNAi screening in glioma stem-like cells identifies PFKFB4 as a key molecule important for cancer cell survival" Oncogene (2012) vol. 31, No. 27, pp. 3235-3243.

(Continued)

*Primary Examiner* — Irina Neagu
(74) *Attorney, Agent, or Firm* — ALGM LLP; Harry J. Guttman

(57) ABSTRACT

Methods and pharmaceutical compositions for inhibiting 6-phosphofructo-2-kinase/fructose-2,6-biphosphatase 4 (PFKFB4) and the treatment of cancer are described.

19 Claims, 21 Drawing Sheets

(56) References Cited

OTHER PUBLICATIONS

Hasemann et al., "The crystal structure of the bifunctional enzyme 6-phosphofructo-2-kinase/fructose-2,6-bisphosphatase reveals distinct domain homologies" Structure (1996) vol. 4, No. 9, pp. 1017-1029.
Jain "Surflex: fully automatic flexible molecular docking using a molecular similarity-based search engine" J Med Chem (2003) vol. 46, No. 4, pp. 499-511.
Kemp et al., "Allosteric regulatory properties of muscle phosphofructokinase" Mol Cell Biochem (1983) vol. 57, No. 2, pp. 147-154.
Kemp et al., "Evolution of the allosteric ligand sites of mammalian phosphofructo-1- kinase" Biochemistry (2002), vol. 41, No. 30, pp. 9426-9430.
Minchenko et al., "Hypoxic regulation of the 6-phosphofructo-2-kinase/fructose-2,6-bisphosphatase gene family (PFKFB-1-4) expression in vivo" FEBS letters (2003) vol. 554, No. 3, pp. 264-270.
Minchenko et al., "6-Phosphofructo-2-kinase/fructose-2,6-bisphosphatase gene family overexpression in human lung tumor" Ukr Biokhim Zh (2005a) vol. 77, No. 6, pp. 46-50.
Minchenko et al., "Expression and hypoxia-responsiveness of 6-phosphofructo-2-kinase/fructose-2,6-bisphosphatase 4 in mammary gland malignant cell lines" Acta biochimica Polonica (2005b) vol. 52, No. 4, pp. 881-888.
Minchenko et al., "Overexpression of 6-phosphofructo-2-kinase/fructose-2,6-bisphosphatase-4 in the human breast and colon malignant tumors" Biochimie (2005c) vol. 87, No. 11, pp. 1005-1010.
Mlakar et al., "Citrate inhibition-resistant form of 6-phosphofructo-1-kinase from Aspergillus niger" Appl Environ Microbiol (2006) vol. 72, No. 7, pp. 4515-4521.
Perez et al., "N-Cinnamoylated Chloroquine Analogues as Dual-Stage Antimalarial Leads" J. Med. Chem. (2013) vol. 56, pp. 556-567.
PubChem Substance record SID 35997106, 5 pages.
PubChem Substance record SID 128585143, 7 pages.
PubChem Substance record SID 236909839, 7 pages.
PubChem Substance record SID 236984397, 7 pages.
Ros et al., "Functional metabolic screen identifies 6-phosphofructo-2-kinase/fructose-2,6-biphosphatase 4 as an important regulator of prostate cancer cell survival" Cancer Discov (2012) vol. 2, No. 4, pp. 328-343.
Sakata et al., "Molecular cloning of the DNA and expression and characterization of rat testes fructose-6-phosphate,2-kinase: fructose-2,6-bisphosphatase" J Biol Chem (1991) vol. 266, No. 24, pp. 15764-15770.
Sali et al., "Comparative protein modeling by satisfaction of spatial restraints" J Mol Biol (1993) vol. 234, No. 3, pp. 779-815.
Sasaki et al., "The cell cycle associated change of the Ki-67 reactive nuclear antigen expression" J Cell Physiol (1987) vol. 133, No. 3, pp. 579-584.
Van Schaftingen et al., "Fructose 2,6-bisphosphate, the probably structure of the glucose- and glucagon-sensitive stimulator of phosphofructokinase" Biochem J (1980a), vol. 192, No. 3, pp. 897-901.
Van Schaftingen et al., "Synthesis of a stimulator of phosphofructokinase, most likely fructose 2,6-bisphosphate, from phosphoric acid and fructose 6-phosphoric acid" Biochem Biophys Res Commun (1980b) vol. 96, No. 4, 1524-1531.
Van Schaftingen et al., "A kinetic study of pyrophosphate: fructose-6-phosphate phosphotransferase from potato tubers. Application to a microassay of fructose 2,6-bisphosphate" Eur J Biochem (1982) vol. 129, No. 1, pp. 191-195.
Yalcin et al., "Nuclear targeting of 6-phosphofructo-2-kinase (PFKFB3) increases proliferation via cyclin-dependent kinases" J Biol Chem (2009a) vol. 284, No. 36, 24223-24232.
Yalcin et al., "Regulation of glucose metabolism by 6-phosphofructo-2-kinase/fructose-2,6-bisphosphatases in cancer" Exp Mol Pathol (2009b) vol. 86, No. 3, pp. 174-179.

Yalcin et al., "6-Phosphofructo-2-kinase (PFKFB3) promotes cell cycle progression and suppresses apoptosis via Cdkl-mediated phosphorylation of p27" Cell death & disease (2014) No. 5, Article e1337, 10 pages.
Ziakas et al., "Nitric oxide releasing derivatives of tolfenamic acid with anti-inflammatory activity and safe gastrointestinal profile" Bioorg. Med. Chem. (2005) vol. 13, pp. 6485-6492.
U.S. Appl. No. 15/568,751 Restriction Requirement dated May 22, 2018, 8 pages.
U.S. Appl. No. 15/568,751 Response to Restriction Requirement action dated Sep. 22, 2018, 6 pages.
U.S. Appl. No. 15/568,751 nonfinal Office action dated Dec. 19, 2018, 23 pages.
U.S. Appl. No. 15/568,751 Response to nonfinal Office action dated Apr. 10, 2019, 16 pages.
U.S. Appl. No. 15/568,751 final Office action dated May 3, 2019, 20 pages.
U.S. Appl. No. 15/568,751 Response to final Office action dated Aug. 1, 2019, 19 pages.
U.S. Appl. No. 15/568,751 nonfinal Office action dated Sep. 19, 2019, 18 pages.
U.S. Appl. No. 15/568,751 Response to nonfinal Office action dated Dec. 18, 2019, 18 pages.
U.S. Appl. No. 15/568,751 Notices of Allowance & Allowability dated Apr. 2, 2020, 11 pages.
U.S. Appl. No. 15/568,751 Notices of Allowance & Allowability dated Nov. 3, 2020, 15 pages.
Johnson et al. (2001) "Relationships between drug activity in NCI preclinical in vitro and in vivo models and early clinical trials" Journal of Cancer, vol. 84, No. 10, pp. 1424-1431.
Sausville et al. (2006) "Contributions of Human Tumor Xenografts to Anticancer Drug Development" Cancer Res., vol. 66, No. 7, pp. 3351-3354.
Williams et al. Faye's Principles of Medicinal Chemistry, 5th edition, pp. 50 and 59-61, 2002.
U.S. Appl. No. 16/170,391 Restriction Requirement dated May 23, 2019, 9 pages.
PubChem Substance record SID 35997106, 5 pages. (2005).
Telang et al. (2015) "Targeting 6-Phosphofructo-2-kInase/Fructose-2,6-BIsphosphatase-4 (PFKFB4) in Cancer" FASEB abstract, vol. 29, No. 1 supplement, Abstract 725.29 (1 page).
U.S. Appl. No. 16/170,391 Response to Restriction Requirement dated Aug. 27, 2019, 6 pages.
U.S. Appl. No. 16/170,391 Nonfinal Office action dated Sep. 13, 2019, 20 pages.
Madrid et al. (2005) "Synthesis of ring-substituted 4-aminoquinolines and evaluation of their antimalarial activities" Bioorg. Med. Chem. Lett., vol. 15, pp. 1015-1018.
PubChem Substance record SID 35997106, 5 pages. (2007).
PubChem Substance record SID 128585143, 7 pages. (2011).
PubChem Substance record SID 236909839, 7 pages. (Feb. 13, 2015).
PubChem Substance record SID 236984397, 7 pages. (Feb. 13, 2015).
CAS database RN 1329224-26-1, 1 page. (2011).
Solomon et al. (2011) "Quinoline as a Privileged Scaffold in Cancer Drug Discovery" Current Medicinal Chemistry, vol. 18, No. 10, pp. 1488-1508.
U.S. Appl. No. 16/170,391 Response to nonfinal Office action dated Dec. 12, 2019, 22 pages.
U.S. Appl. No. 16/170,391 final Office action dated Feb. 10, 2020, 14 pages.
U.S. Appl. No. 16/170,391 Response to final Office action dated Apr. 13, 2020, 18 pages.
U.S. Appl. No. 16/170,391 Notices of Allowance & Allowability dated Apr. 24, 2020, 12 pages.
Okuno et al., Chemical Abstracts 153:580355—Abstract of US 20100273841, 2 pages. (2010).
Telang et al. (2015) "Targeting 6-Phosphofructo-2-kInase/Fructose-2,6-BIsphosphatase-4 (PFKFB4) in Cancer" FASEB abstract, vol. 29, No. 1 supplement, Abstract 725.29 (1 page).

* cited by examiner

A

B

C

D

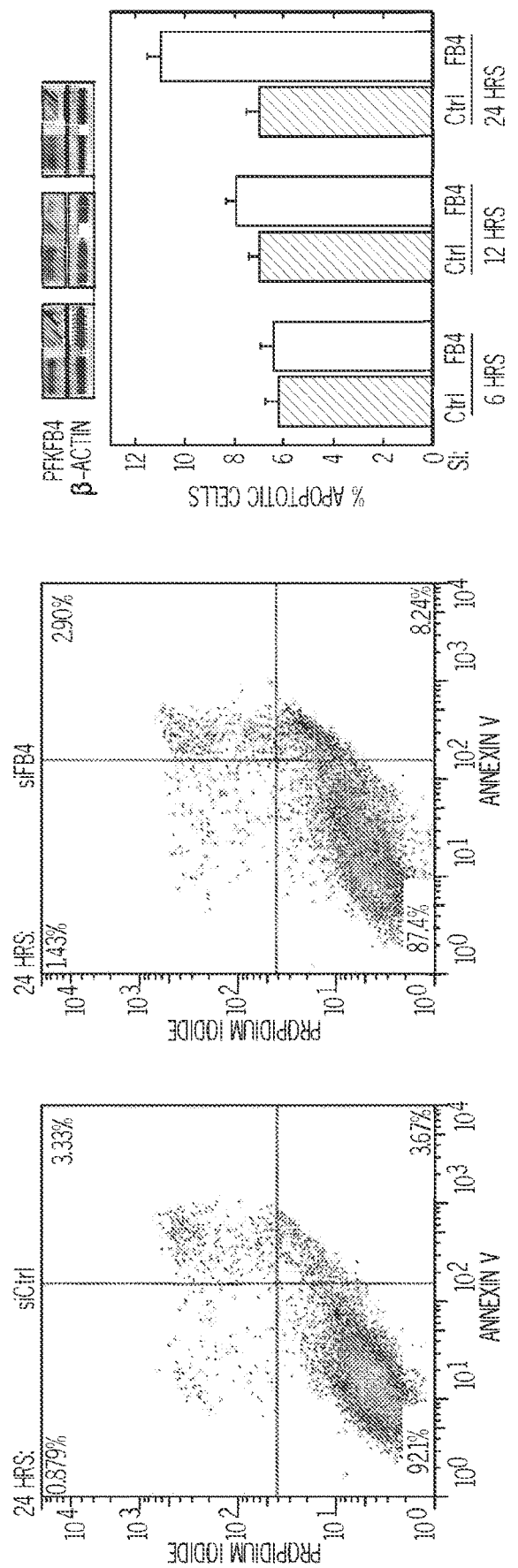

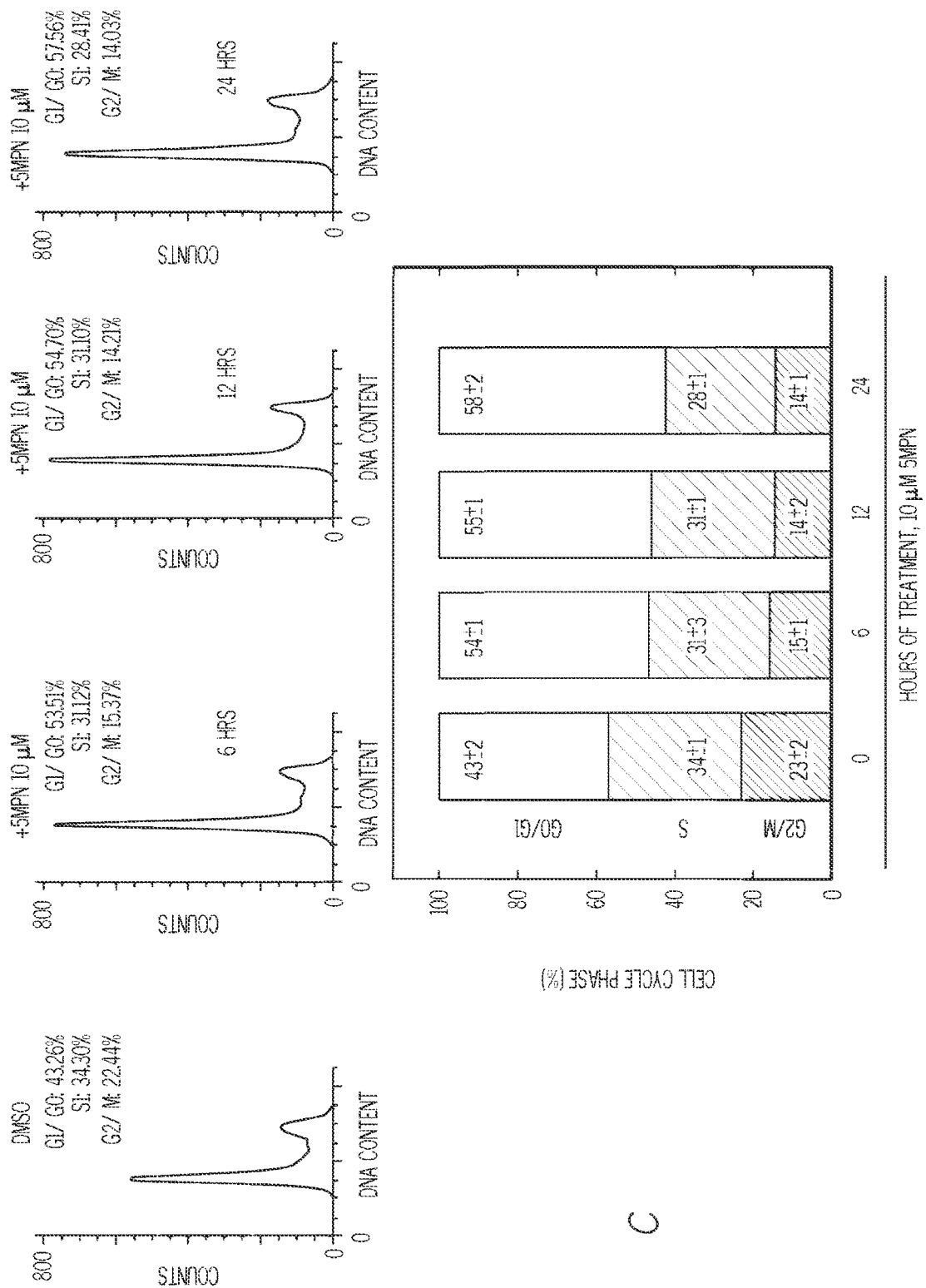

D

E

F

A

| DOSING | t₁/₂ | C0 (ng/ml) | AUC last (hr.ng/ml) | AUC inf (hr.ng/ml) | AUC EXTR (%) | Vss (L/kg) | CL (mL/min/kg) | MRT (h) |
|---|---|---|---|---|---|---|---|---|
| I.V. | 0.387 | 249 | 111 | 114 | 2.49 | 8.48 | 291 | 0.485 |

| DOSING | t₁/₂ | Cmax (ng/ml) | AUC last (hr.ng/ml) | AUC inf (hr.ng/ml) | AUC EXTR (%) | Vss (L/kg) | F (mL/min/kg) | MRT (h) |
|---|---|---|---|---|---|---|---|---|
| P.O | 1.67 | 98.7 | 225 | 234 | 3.78 | 8.48 | 40.9 | 2.31 |

B

C

D

E

F

G

DMSO | 5MPN

H

J

K

A           B

COMPOUNDS FOR THE TREATMENT OF CANCER

CROSS-REFERENCE TO RELATED APPLICATIONS

This application is a Divisional of U.S. patent application Ser. No. 15/568,751 filed Oct. 23, 2017, entitled "SELECTIVE PFKFB4 INHIBITORS FOR THE TREATMENT OF CANCER" which is herein incorporated by reference in its entirety, and which is a National Stage Entry of International Application No. PCT/US2016/028868 filed Apr. 22, 2016, entitled "SELECTIVE PFKFB4 INHIBITORS FOR THE TREATMENT OF CANCER" which is herein incorporated by reference in its entirety, and which claims the benefit of U.S. Provisional Application No. 62/152,239, filed Apr. 24, 2015, entitled "SELECTIVE PFKFB4 INHIBITORS FOR THE TREATMENT OF CANCER" which is herein incorporated by reference in its entirety.

TECHNICAL FIELD

The presently disclosed subject matter relates to methods, compounds, and pharmaceutical compositions for the treatment of cancer. More particularly, the presently disclosed subject matter relates to the use of compounds for the selective inhibition of 6-phosphofructo-2-kinase/fructose-2,6-biphosphatase 4 (PFKFB4). Methods of using said compounds to reduce glycolytic flux, reduce the proliferative capacity of a cell, reduce fructose-2,6-bisphosphate (F2,6BP), and to treat cancer are described.

BACKGROUND

Neoplastic cells preferentially utilize glycolysis to satisfy their increased needs for energy and biosynthetic precursors. The PFKFB enzymes (PFKFB 1-4) synthesize fructose-2,6-bisphosphate (F2,6BP). F2,6BP activates 6-phosphofructo-1-kinase (PFK-1), an essential control point in the glycolytic pathway. Until recently, the PFKFB3 isozyme has been considered the principal source of the increased F2,6BP observed in cancer cells. However, new evidence indicates the co-expression of several PFKFB isozymes in transformed and untransformed tissues, as well as increased expression of the PFKFB4 isoform in several neoplastic cell lines and in tumors.

Accordingly, there remains a need in the art for PFKFB4 inhibitors and methods of using the same that can effectively be used to target neoplastic cells, including the mechanisms within those cells that relate to the preferential use of the glycolytic pathway. More specifically, there remains a need in the art for small molecule PFKFB4 inhibitors that can pharmacologically disrupt the kinase domain of PFKFB4 and therefore decrease the glucose metabolism and growth of human cancers. Importantly, the PFKFB4 inhibitors should be selective for PFKFB4, and should not directly inhibit PFKFB1, PFKFB2, and PFKFB3. Furthermore, the PFKFB4 inhibitor should have good oral bioavailability while avoiding toxicity.

SUMMARY

Accordingly, the presently disclosed subject matter relates to the use of compounds for the selective inhibition of PFKFB4. Methods of using said compounds to reduce glycolytic flux, reduce the proliferative capacity of a cell, reduce fructose-2,6-bisphosphate (F2,6BP), and to treat cancer are disclosed herein.

One embodiment of the presently-disclosed subject matter is directed to a method of treating cancer in a subject in need of treatment thereof, the method comprising administering to the subject an effective amount of a compound of:

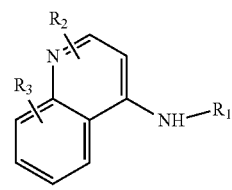

(I)

wherein:
$R_1$ is a $C_1$-$C_5$ alkyl nitrooxy;
$R_2$ can be present or absent, and when present is a $C_1$-$C_5$ alkyl;
$R_3$ can be present or absent, and when present is a $C_1$-$C_5$ alkoxy; and
wherein if $R_2$ is present and located on the nitrogen of the quinoline group, said nitrogen has a positive charge.

Another embodiment of the presently-disclosed subject matter is directed to a method of treating cancer in a subject in need of treatment thereof, the method comprising administering to the subject an effective amount of a compound of:

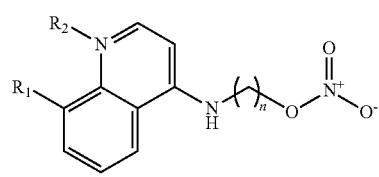

(II)

wherein:
n is 1-5;
$R_1$ can be present or absent, and when present is a $C_1$-$C_5$ alkoxy;
$R_2$ can be present or absent, and when present is a $C_1$-$C_5$ alkyl; and
wherein if $R_2$ is present and located on the nitrogen of the quinoline group, said nitrogen has a positive charge.

One embodiment of the presently-disclosed subject matter is directed to a method of treating cancer in a subject in need of treatment thereof, the method comprising administering to the subject an effective amount of a compound of:

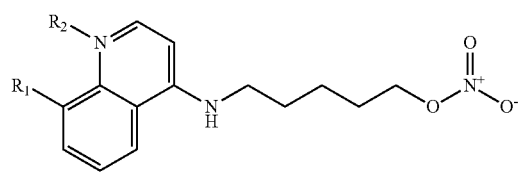

(III)

wherein:
$R_1$ can be present or absent, and when present is a $C_1$-$C_5$ alkoxy;

$R_2$ can be present or absent, and when present is a $C_1$-$C_5$ alkyl; and wherein if $R_2$ is present, the nitrogen of the quinoline group has a positive charge.

A further embodiment of the presently-disclosed subject matter is directed to a method of treating cancer in a subject in need of treatment thereof, the method comprising administering to the subject an effective amount of a compound of:

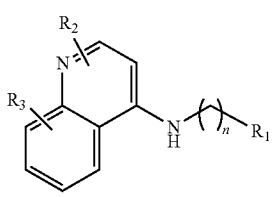
(IV)

wherein:

n is 1-6;

$R_1$ is carboxylic acid, methyl sulfonamide (-NH-SO$_2$-CH$_3$), carboxylic acid methyl ester, hydroxide, nitrate, or tert-butyl carbamate;

$R_2$ can be present or absent, and when present is a $C_1$-$C_5$ alkyl;

$R_3$ can be present or absent, and when present is a $C_1$-$C_5$ alkoxy, chloride, or hydrogen; and wherein if $R_2$ is present and located on the nitrogen of the quinoline group, said nitrogen has a positive charge.

Another embodiment of the presently-disclosed subject matter is directed to a method of treating cancer in a subject in need of treatment thereof, the method comprising administering to the subject an effective amount of a compound of:

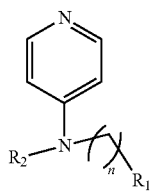
(V)

wherein:

n is 1-6;

$R_1$ nitrate; and $R_2$ is a hydrogen or nitrogen dioxide.

One embodiment of the presently-disclosed subject matter is directed to a method of treating cancer in a subject in need of treatment thereof, the method comprising administering to the subject an effective amount of a compound 5-[(8-methoxyquinolin-4-yl)amino]pentyl nitrate (5MPN).

An additional embodiment of the presently-disclosed subject matter is directed to a method of treating cancer in a subject in need of treatment thereof, the method comprising administering to the subject an effective amount of a compound 5-[(8-methoxyl-methylquinolin-1-ium-4-yl)amino]pentyl nitrate (MPN-2).

An additional embodiment is directed to a method of inhibiting PFKFB4 in a cell, the method comprising contacting the cell with an effective amount of a compound of:

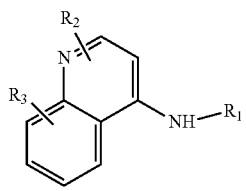
(I)

wherein:

$R_1$ is a $C_1$-$C_5$ alkyl nitrooxy;

$R_2$ can be present or absent, and when present is a $C_1$-$C_5$ alkyl;

$R_3$ can be present or absent, and when present is a $C_1$-$C_5$ alkoxy; and wherein if $R_2$ is present and located on the nitrogen of the quinoline group, said nitrogen has a positive charge.

A further embodiment is directed to a method of inhibiting PFKFB4 in a cell, the method comprising contacting the cell with an effective amount of a compound of:

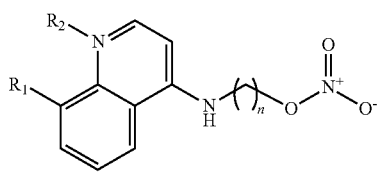
(II)

wherein:

n is 1-5;

$R_1$ can be present or absent, and when present is a $C_1$-$C_5$ alkoxy;

$R_2$ can be present or absent, and when present is a $C_1$-$C_5$ alkyl; and wherein if $R_2$ is present and located on the nitrogen of the quinoline group, said nitrogen has a positive charge.

An additional embodiment is directed to a method of inhibiting PFKFB4 in a cell, the method comprising contacting the cell with an effective amount of a compound of:

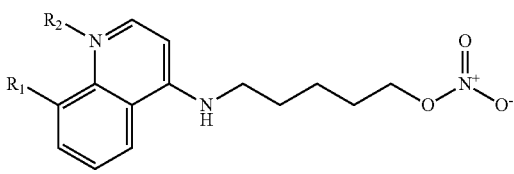
(III)

wherein:

$R_1$ can be present or absent, and when present is a $C_1$-$C_5$ alkoxy;

$R_2$ can be present or absent, and when present is a $C_1$-$C_5$ alkyl; and wherein if $R_2$ is present, the nitrogen of the quinoline group has a positive charge.

A further embodiment of the presently-disclosed subject matter is directed to a method of inhibiting PFKFB4 in a cell, the method comprising contacting the cell with an effective amount of a compound of:

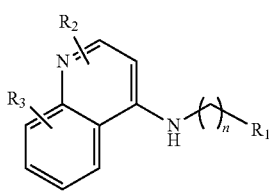

wherein:
n is 1-6;
R$_1$ is carboxylic acid, methyl sulfonamide (-NH-SO$_2$-CH$_3$), carboxylic acid methyl ester, hydroxide, nitrate, or tert-butyl carbamate;
R$_2$ can be present or absent, and when present is a C$_1$-C$_5$ alkyl;
R$_3$ can be present or absent, and when present is a C$_1$-C$_5$ alkoxy, chloride, or hydrogen; and
wherein if R$_2$ is present and located on the nitrogen of the quinoline group, said nitrogen has a positive charge.

Another embodiment of the presently-disclosed subject matter is directed to a method of inhibiting PFKFB4 in a cell, the method comprising contacting the cell with an effective amount of a compound of:

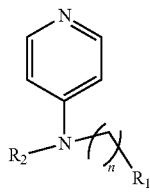

wherein:
n is 1-6;
R$_1$ nitrate; and
R$_2$ is a hydrogen or nitrogen dioxide.

Another embodiment is directed to a method of inhibiting PFKFB4 in a cell, the method comprising contacting the cell with an effective amount of 5MPN.

A further embodiment is directed to a method of inhibiting PFKFB4 in a cell, the method comprising contacting the cell with an effective amount of MPN-2.

One embodiment is directed to a method of inhibiting PFKFB4 in a subject, the method comprising administering to the subject an effective amount of a compound of:

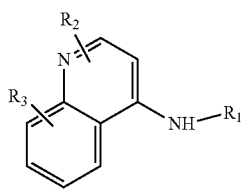

wherein:
R$_1$ is a C$_1$-C$_5$ alkyl nitrooxy;
R$_2$ can be present or absent, and when present is a C$_1$-C$_5$ alkyl;
R$_3$ can be present or absent, and when present is a C$_1$-C$_5$, alkoxy; and wherein if R$_2$ is present and located on the nitrogen of the quinoline group, said nitrogen has a positive charge.

One embodiment is directed to a method of inhibiting PFKFB4 in a subject, the method comprising administering to the subject an effective amount of a compound of:

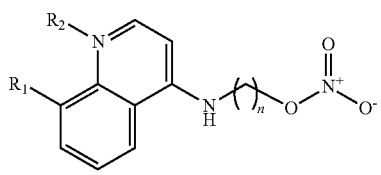

wherein:
n is 1-5;
R$_1$ can be present or absent, and when present is a C$_1$-C$_5$ alkoxy;
R$_2$ can be present or absent, and when present is a C$_1$-C$_5$ alkyl; and
wherein if R$_2$ is present and located on the nitrogen of the quinoline group, said nitrogen has a positive charge.

One embodiment is directed to a method of inhibiting PFKFB4 in a subject, the method comprising administering to the subject an effective amount of a compound of:

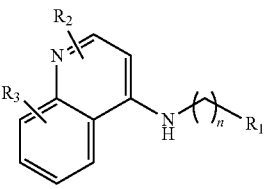

wherein:
R$_1$ can be present or absent, and when present is a C$_1$-C$_5$ alkoxy;
R$_2$ can be present or absent, and when present is a C$_1$-C$_5$ alkyl; and
wherein if R$_2$ is present, the nitrogen of the quinoline group has a positive charge.

A further embodiment of the presently-disclosed subject matter is directed to a method of inhibiting PFKFB4 in a subject, the method comprising contacting the cell with an effective amount of a compound of:

(IV)

wherein:
n is 1-6;
R$_1$ is carboxylic acid, methyl sulfonamide (-NH-SO$_2$-CH$_3$), carboxylic acid methyl ester, hydroxide, nitrate, or tert-butyl carbamate;
R$_2$ can be present or absent, and when present is a C$_1$-C$_5$ alkyl;

$R_3$ can be present or absent, and when present is a $C_1$-$C_5$ alkoxy, chloride, or hydrogen; and wherein if $R_2$ is present and located on the nitrogen of the quinoline group, said nitrogen has a positive charge.

Another embodiment of the presently-disclosed subject matter is directed to a method of inhibiting PFKFB4 in a subject, the method comprising contacting the cell with an effective amount of a compound of:

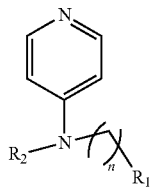

(V)

wherein:

n is 1-6;

$R_1$ nitrate; and $R_2$ is a hydrogen or nitrogen dioxide.

A further embodiment is directed to a method of inhibiting PFKFB4 in a subject, the method comprising administering to the subject an effective amount of 5MPN.

Another embodiment is directed to a method of inhibiting PFKFB4 in a subject, tire method comprising administering to the subject an effective amount of MPN-2.

An additional embodiment is directed to a method of reducing glycolytic flux in a cell, the method comprising contacting the cell with an effective amount of a compound of:

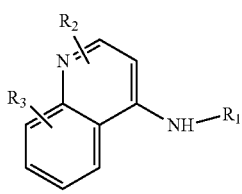

(I)

wherein:

$R_1$ is a $C_1$-$C_5$ alkyl nitrooxy;

$R_2$ can be present or absent, and when present is a $C_1$-$C_5$ alkyl;

$R_3$ can be present or absent, and when present is a $C_1$-$C_5$ alkoxy; and wherein if $R_2$ is present and located on the nitrogen of the quinoline group, said nitrogen has a positive charge.

One embodiment is directed to a method of reducing glycolytic flux in a cell, the method comprising contacting the cell with an effective amount of a compound of:

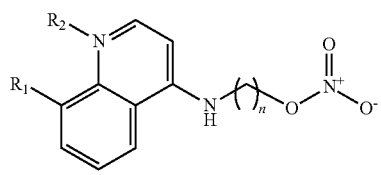

(II)

wherein:

n is 1-5;

$R_1$ can be present or absent, and when present is a $C_1$-$C_5$ alkoxy;

$R_2$ can be present or absent, and when present is a $C_1$-$C_5$ alkyl; and wherein if $R_2$ is present and located on the nitrogen of the quinoline group, said nitrogen has a positive charge.

An additional embodiment is directed to a method of reducing glycolytic flux in a cell, the method comprising contacting the cell with an effective amount of a compound of:

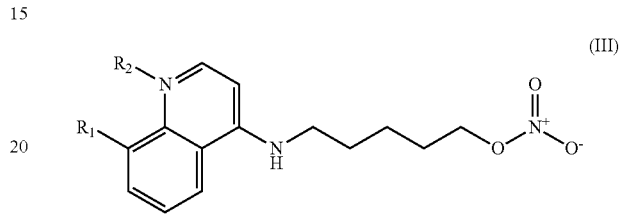

(III)

wherein:

$R_1$ can be present or absent, and when present is a $C_1$-$C_5$ alkoxy;

$R_2$ can be present or absent, and when present is a $C_1$-$C_5$ alkyl; and wherein if $R_2$ is present, the nitrogen of the quinoline group has a positive charge.

An additional embodiment is directed to a method of reducing glycolytic flux in a cell, the method comprising contacting the cell with an effective amount of 5MPN.

One embodiment is directed to a method of reducing glycolytic flux in a cell, the method comprising contacting the cell with an effective amount of MPN-2.

An additional embodiment is directed to a method of reducing proliferative capacity of a cell, the method comprising contacting the cell with an effective amount of a compound of:

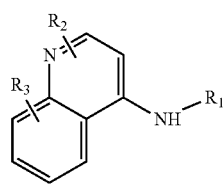

(I)

wherein:

$R_1$ is a $C_1$-$C_5$ alkyl nitrooxy;

$R_2$ can be present or absent, and when present is a $C_1$-$C_5$ alkyl;

$R_3$ can be present or absent, and when present is a $C_1$-$C_5$ alkoxy; and wherein if $R_2$ is present and located on the nitrogen of the quinoline group, said nitrogen has a positive charge.

A further embodiment is directed to a method of reducing proliferative capacity of a cell, the method comprising contacting the cell with an effective amount of a compound of:

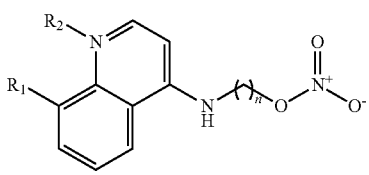

(II)

wherein:
n is 1-5;
R$_1$ can be present or absent, and when present is a C$_1$-C$_5$ alkoxy;
R$_2$ can be present or absent, and when present is a C$_1$-C$_5$ alkyl; and
wherein if R$_2$ is present and located on the nitrogen of the quinoline group, said nitrogen has a positive charge.

An additional embodiment is directed to a method of reducing proliferative capacity of a cell, the method comprising contacting the cell with an effective amount of a compound of:

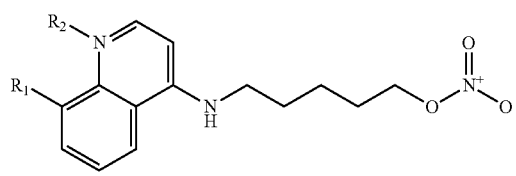

(III)

wherein:
R$_1$ can be present or absent, and when present is a C$_1$-C$_5$ alkoxy;
R$_2$ can be present or absent, and when present is a C$_1$-C$_5$ alkyl; and
wherein if R$_2$ is present, the nitrogen of the quinoline group has a positive charge.

A further embodiment of the presently-disclosed subject matter is directed to a method of reducing proliferative capacity of a cell, the method comprising contacting the cell with an effective amount of a compound of:

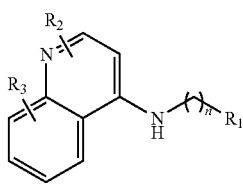

(IV)

wherein:
n is 1-6;
R$_1$ is carboxylic acid, methyl sulfonamide (-NH-SO$_2$-CH$_3$), carboxylic acid methyl ester, hydroxide, nitrate, or tert-butyl carbamate;
R$_2$ can be present or absent, and when present is a C$_1$-C$_5$ alkyl;
R$_3$ can be present or absent, and when present is a C$_1$-C$_5$ alkoxy, chloride, or hydrogen; and
wherein if R$_2$ is present and located on the nitrogen of the quinoline group, said nitrogen has a positive charge.

Another embodiment of the presently-disclosed subject matter is directed to a method of reducing proliferative capacity of a cell, the method comprising contacting the cell with an effective amount of a compound of:

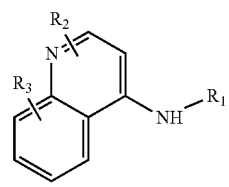

(V)

wherein:
n is 1-6;
R$_1$ nitrate; and
R$_2$ is a hydrogen or nitrogen dioxide.

One embodiment is directed to a method of reducing proliferative capacity of a cell, the method comprising contacting the cell with an effective amount of 5MPN.

Another embodiment is directed to a method of reducing proliferative capacity of a cell, the method comprising contacting the cell with an effective amount of MPN-2.

An additional embodiment is directed to a method of reducing fructose-2,6-bisphosphate (F2,6BP) in a cell, the method comprising contacting the cell with an effective amount of a compound of:

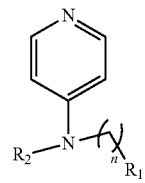

(I)

wherein:
R$_1$ is a C$_1$-C$_5$ alkyl nitrooxy;
R$_2$ can be present or absent, and when present is a C$_1$-C$_5$ alkyl;
R$_3$ can be present or absent, and when present is a C$_1$-C$_5$ alkoxy; and
wherein if R$_2$ is present and located on the nitrogen of the quinoline group, said nitrogen has a positive charge.

A further embodiment is directed to a method of reducing fructose-2,6-bisphosphate (F2,6BP) in a cell, the method comprising contacting the cell with an effective amount of a compound of:

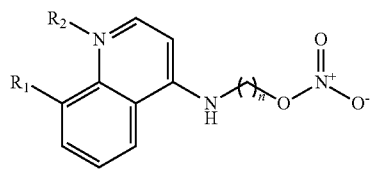

(II)

wherein:
n is 1-5;
R$_1$ can be present or absent, and when present is a C$_1$-C$_5$ alkoxy;

$R_2$ can be present or absent, and when present is a $C_1$-$C_5$ alkyl; and wherein if $R_2$ is present and located on the nitrogen of the quinoline group, said nitrogen has a positive charge.

An additional embodiment is directed to a method of reducing fructose-2,6-bisphosphate (F2,6BP) in a cell, the method comprising contacting the cell with an effective amount of a compound of:

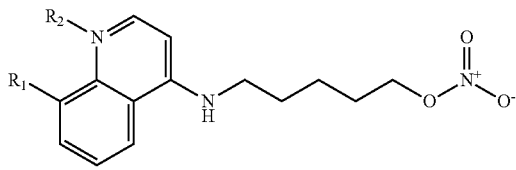

(III)

wherein:

$R_1$ can be present or absent, and when present is a $C_1$-$C_5$ alkoxy;

$R_2$ can be present or absent, and when present is a $C_1$-$C_5$ alkyl; and wherein if $R_2$ is present, the nitrogen of the quinoline group has a positive charge.

A further embodiment is directed to a method of reducing fructose-2,6-bisphosphate (F2,6BP) in a cell, the method comprising contacting the cell with an effective amount of 5MPN.

An additional embodiment is directed to a method of reducing fructose-2,6-bisphosphate (F2,6BP) in a cell, the method comprising contacting the cell with an effective amount of MPN-2.

An additional embodiment is directed to a pharmaceutical composition comprising an effective amount of a compound of:

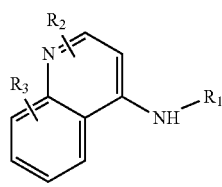

(I)

wherein:

$R_1$ is a $C_1$-$C_5$ alkyl nitrooxy;

$R_2$ can be present or absent, and when present is a $C_1$-$C_5$ alkyl;

$R_3$ can be present or absent, and when present is a $C_1$-$C_5$ alkoxy; and wherein if $R_2$ is present and located on the nitrogen of the quinoline group, said nitrogen has a positive charge; and and at least one pharmaceutical excipient.

One embodiment is directed to a pharmaceutical composition comprising an effective amount of a compound of:

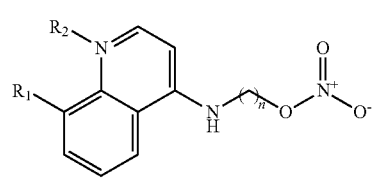

(II)

wherein:

n is 1-5;

$R_1$ can be present or absent, and when present is a $C_1$-$C_5$ alkoxy;

$R_2$ can be present or absent, and when present is a $C_1$-$C_5$ alkyl; and wherein if $R_2$ is present and located on the nitrogen of the quinoline group, said nitrogen has a positive charge; and and at least one pharmaceutical excipient.

An additional embodiment is directed to a pharmaceutical composition comprising an effective amount of a compound of:

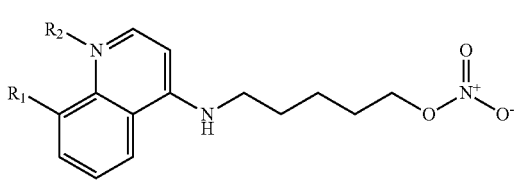

(III)

wherein:

$R_1$ can be present or absent, and when present is a $C_1$-$C_5$ alkoxy;

$R_2$ can be present or absent, and when present is a $C_1$-$C_5$ alkyl; and wherein if $R_2$ is present, the nitrogen of the quinoline group has a positive charge; and and at least one pharmaceutical excipient.

A further embodiment of the presently-disclosed subject matter is directed to a pharmaceutical composition comprising an effective amount of a compound of:

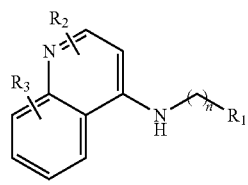

(IV)

wherein:

n is 1-6;

$R_1$ is carboxylic acid, methyl sulfonamide (-NH-SO$_2$-CH$_3$), carboxylic acid methyl ester, hydroxide, nitrate, or tert-butyl carbamate;

$R_2$ can be present or absent, and when present is a $C_1$-$C_5$ alkyl;

$R_3$ can be present or absent, and when present is a $C_1$-$C_5$ alkoxy, chloride, or hydrogen; and wherein if $R_2$ is present and located on the nitrogen of the quinoline group, said nitrogen has a positive charge; and and at least one pharmaceutical excipient.

Another embodiment of the presently-disclosed subject matter is directed to a pharmaceutical composition comprising an effective amount of a compound of:

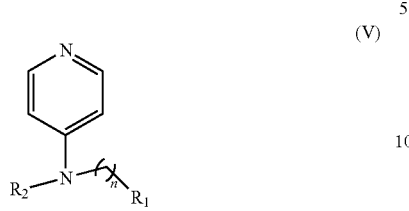

(V)

wherein:
n is 1-6;
$R_1$ nitrate; and
$R_2$ is a hydrogen or nitrogen dioxide;
and at least one pharmaceutical excipient.

An additional embodiment is directed to a pharmaceutical composition comprising an effective amount of 5MPN, and at least one pharmaceutical excipient.

A further embodiment is directed to a pharmaceutical composition comprising an effective amount of MPN-2, and at least one pharmaceutical excipient.

An additional embodiment of the presently-disclosed subject matter is directed to a compound of Formula (IV):

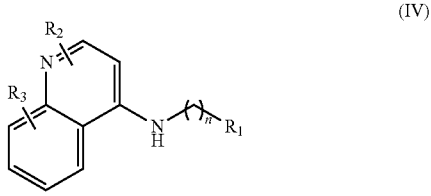

(IV)

wherein:
n is 1-6;
$R_1$ is carboxylic acid, methyl sulfonamide (-NH-$SO_2$-$CH_3$), carboxylic acid methyl ester, hydroxide, nitrate, or tert-butyl carbamate;
$R_2$ can be present or absent, and when present is a $C_1$-$C_5$ alkyl;
$R_3$ can be present or absent, and when present is a $C_1$-$C_5$ alkoxy, chloride, or hydrogen; and
wherein if $R_2$ is present and located on the nitrogen of the quinoline group, said nitrogen has a positive charge.

Another embodiment of the presently-disclosed subject matter is directed to a compound of Formula (V):

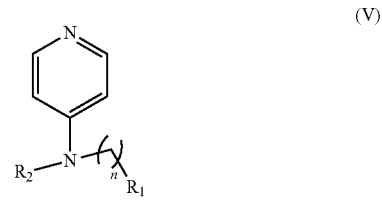

(V)

wherein:
n is 1-6;
$R_1$ nitrate; and
$R_2$ is a hydrogen or nitrogen dioxide.

These and additional aspects and features of the instant invention will be clarified by reference to the figures and detailed description set forth herein.

BRIEF DESCRIPTION OF THE DRAWINGS

FIG. 1A shows a schematic representation of the 5MPN molecule docked in the crystal structure of rat testes PFKFB4. 5MPN is shown in thicker stick representation than the surrounding protein residues. FIG. 1B shows the molecular structure of 5MPN (MW, 305.3 kDa). FIG. 1C and FIG. 1D show Michaelis-Menten and Lineweaver-Burk double reciprocal plots, respectively, examining PFKFB4 enzyme activity as a function of F6P concentration (0-2000 μmol/L). In vitro kinase assays using purified recombinant human PFKFB4 were performed as described in the presence or absence of 0, 0.1, 1 or 10 μM 5MPN. Data shown are representative of three independent experiments.

FIG. 2A shows die results of H460 NSCLC cells treated with DMSO±10 μM 5MPN. The effects on F2,6BP production, glycolysis and ATP were measured after 6-72 hours. FIG. 2B shows the proliferation of H460 cells exposed to DMSO±5MPN after 24-72 hours. FIG. 2C shows the cell growth of NHBE cells and indicated transformed cell lines that were exposed to DMSO±5MPN. Viable cells counted at 48 hours. FIG. 2D shows cell growth of NHBE and hT/LT/Ras cells treated with DMSO±5MPN. Live cells were counted at 48 hours. (*p value<0.01 hT/LT/Ras vs. NHBE). FIG. 2E, shows PFKFB4 expression of H460 cells transfected with empty pCMV-XL4 (Vec) or pCMV-XL4 containing full-length PFKFB4 (FB4) for 24 hours that were treated with DMSO±10 μM 5MPN. 24 hours after treatment with DMSO±10 μM 5MPN, PFKFB4 expression was examined by Western blot and viable cells were counted. (*p value<0.01 Vec vs. FB4 exposed to 5MPN). FIG. 2F shows large T antigen-immortalized, tamoxifen (4HT)-inducible PFKFB4$^{-/-}$ lung fibroblasts that were exposed to vehicle (ethanol)±10 μM 4HT for 24 hours and then treated with DMSO±10 μM 5MPN. Cell counts and PFKFB4 protein expression were examined 24 hours later. (*p value<0.01 vehicle vs. +4HT, exposed to 5MPN). Data are expressed as the mean±SD of three experiments.

FIG. 3A shows H460 cells treated with DMSO±10 μM 5MPN, while FIG. 3B shows H460 cells treated transfected with nonsense (siCtrl) or PFKFB4 siRNA (siFB4). Cells were analyzed for induction of apoptosis by flow cytometry. Decrease in PFKFB4 protein expression by siFB4 was confirmed by Western blot. PI$^+$+PI/Ann V$^+$ cells shown as % apoptotic cells. FIG. 3C shows H460 cells treated with DMSO±10 μM 5MPN and the distribution of cells in G1, S and G2 phases of the cell cycle. FIG. 3D shows H460 cells transfected with siCtrl or siFB4 and the distribution of cells in phases of the cell cycle, H460 cells were transfected with empty pCMV-XL4 (Vec) or pCMV-XL4 containing PFKFB4 (FB4) for 24 hours then treated with DMSO±10 μM 5MPN for 24 hours. FIG. 3E shows H460 cells transfected with siCtrl or siFB4 and PFKFB4 protein expression and F2,6BP concentration, H460 cells were transfected with empty pCMV-XL4 (Vec) or pCMV-XL4 containing PFKFB4 (FB4) for 24 hours then treated with DMSO±10 μM 5MPN for 24 hours. (*p value<0.01 Vec vs. FB4 exposed to 5MPN.) FIG. 3F shows H460 cells transfected with siCtrl or siFB4 and the distribution of cells in G1, S and G2 phases of the cell cycle. Data shown are representative of three independent experiments and are expressed as the mean±SD of three experiments. *p value<0.01 compared to control.

FIG. 4A and FIG. 4B show the oral and intravenous pharmacokinetic properties of 5MPN were in C57BL/6 mice. Groups of 10 C57BL/6 mice were implanted with LLC cells and, when tumors reached a mass of 150-200 mg, were randomized to daily administration of DMSO or 5MPN by gavage (120 mg/kg, for two weeks). FIG. 4C and FIG. 4D show daily tumor and daily body mass measurements, respectively. FIG. 4E shows F2,6BP expression after 10 days of daily administration of DMSO or 5MPN (120 mg/kg) by gavage. The mice were euthanized, and tumors extracted and analyzed for F2,6BP (shown as % of DMSO). FIG. 4F shows micro-PET scans obtains from separate groups of tumor-bearing mice that were administered either DMSO or 5MPN (120 mg/kg by gavage, once). Regions of interest in the tumor and cerebellum were quantified in quadruplicate. Representative transverse view cuts are shown with red arrows indicating the tumor. FIG. 4G shows the in vitro cell cycle analysis of LLC cells that were exposed to DMSO±10 µM 5MPN through the examination of Ki67-positive cells. FIG. 4H shows Ki67 staining in LLC xenographs that were examined by immunohistochemistry (representative sections shown. 10× and 25× magnification). Groups of 10 C57BL/6 mice were implanted with LLC cells and, when tumors reached a mass of 150-200 mg, were randomized to daily administration of DMSO or 5MPN by gavage (120 mg/kg, for two weeks). FIG. 4I shows Ki67 positive pixels that were enumerated in a minimum of 5 fields per tumor section. Groups of 10 C57BL/6 mice were implanted with LLC cells and, when tumors reached a mass of 150-200 mg, were randomized to daily administration of DMSO or 5MPN by gavage (120 mg/kg, for two weeks). FIG. 4J and FIG. 4K show tumor and body mass measurements (collected daily), respectively, of groups of 10 BALB/c athymic mice implanted with H460 NSCLC cells and, when tumors were 150-200 mg, were randomized to daily DMSO or 5MPN by gavage. *p value<0.01 compared to controls.

FIG. 5A shows the molecular structure of MPN-2. FIG. 5B shows that MPN-2 significantly inhibits PFKFB4 activity. FIG. 5C shows that MPN-2 significantly inhibits F2,6BP production. FIG. 5D shows that MPN-2 decreases the proliferation of a human cancer cell line, H460 NSCLC cells. Viable cells counted at 48 hours and at 72 hours. FIG. 5E shows the oral and intravenous pharmacokinetic properties of MPN-2 in CD-1 mice (N=3).

FIG. 6A and FIG. 6B shows the results of H460 NSCLC cells treated with DMSO±the indicated concentrations of MPN-2. The effects on glycolysis (FIG. 6A) and ATP (FIG. 6B) were measured after 48 hours. FIG. 6C shows that MPN-2 decreases the proliferation of MCF7, SK-BR-3, H460, and A549 cells exposed to DMSO±the indicated concentrations of MPN-2 after 24-72 hours (72 hours shown). FIG. 6D show daily tumor mass measurements of groups of 10 C57BL/6 mice that were implanted with LLC cells and, when tumors reached a mass of 150-200 mg, were randomized to daily administration of DMSO or 5MPN in DMSO at the indicated dose by intraperitoneal injection (10 mg/kg, for eleven days).

FIG. 7 shows the results of H460 NSCLC cells treated with DMSO±the indicated concentrations of two compounds of Formula IV at the indicated doses. Specifically, FBR1-02 corresponds to

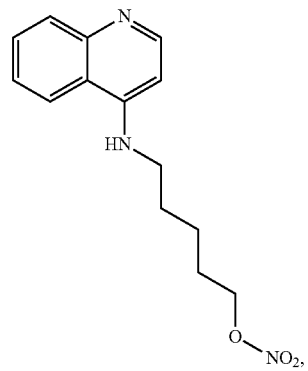 [SMILES: O=[N+]([O-])OCCCCCNc1ccnc2ccccc12]

while FBR1-09 corresponds to

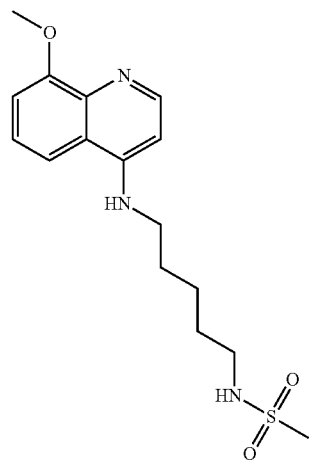

Figure 8:
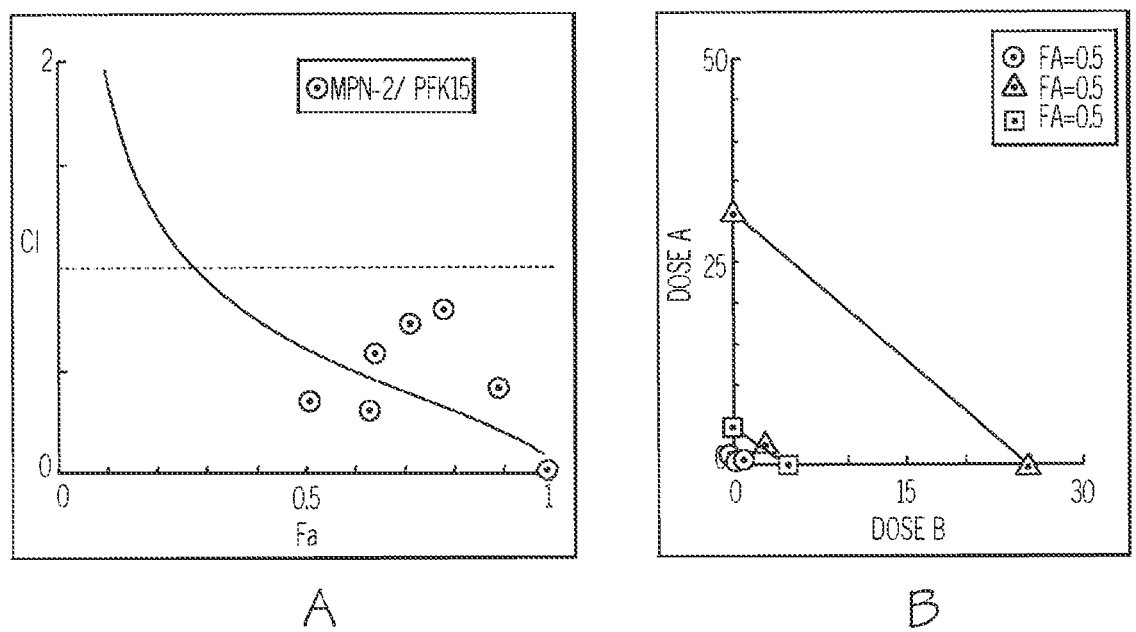

FIG. 8. Dual PFKFB4 and PFKFB3 inhibition with MPN-2 and PFK15, respectively, causes a synergistic increase in cell death. FIG. 8A shows the Fa-Cl combination index plot, while FIG. 8B shows the isobologram.

Figure 9:
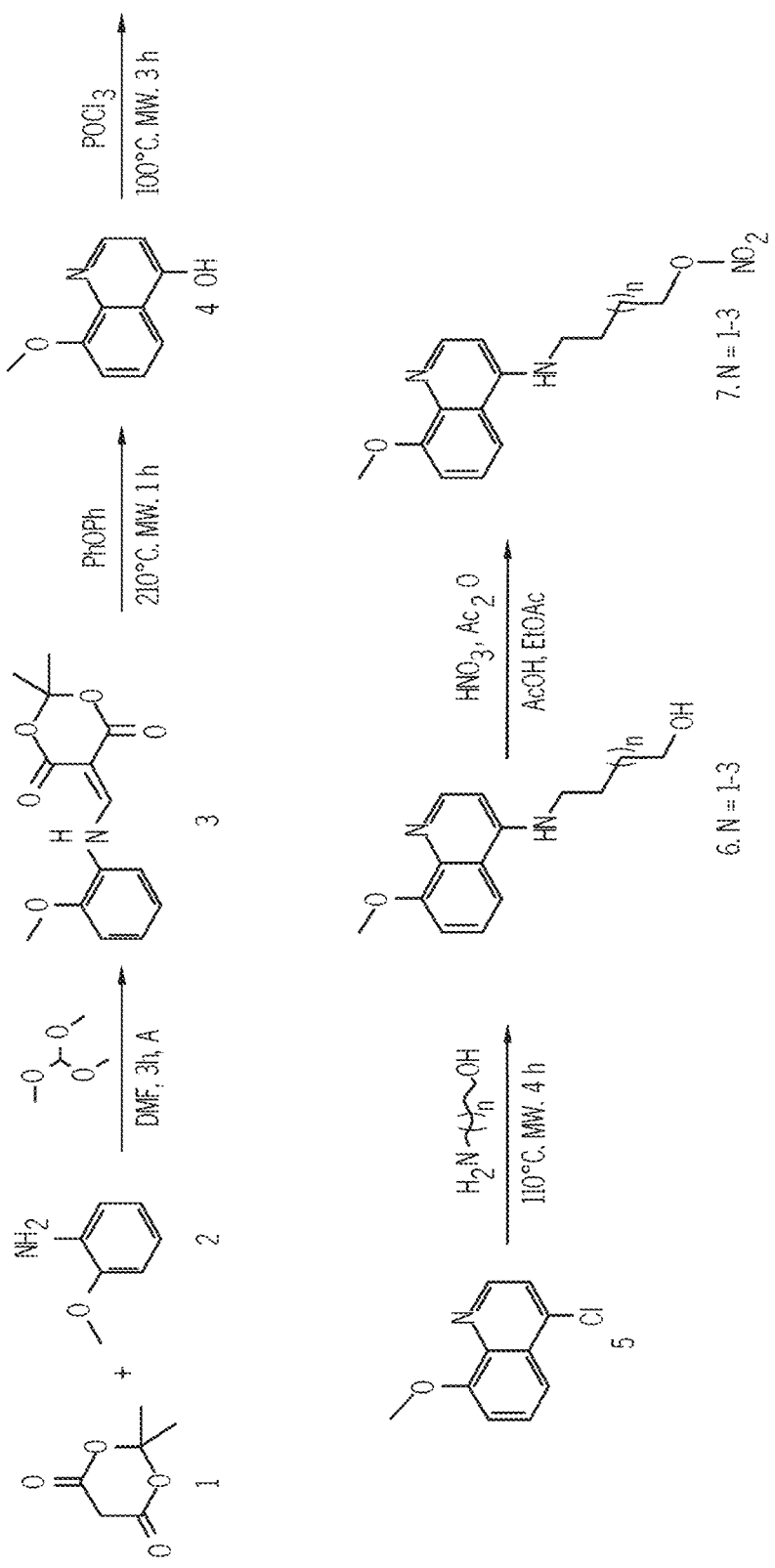

FIG. 9. Synthesis pathway of the small molecule antagonists of the kinase domain of PFKFB4. FIG. 9 shows a synthesis pathway used to create various compounds of Formulae (I), (II), and (III), (IV), (V), (VI), and (VII)).

DETAILED DESCRIPTION

Particular details of various embodiments of the invention are set forth to illustrate certain aspects and not to limit the scope of the invention. It will be apparent to one of ordinary skill in the art that modifications and variations are possible without departing from the scope of the embodiments defined in the appended claims. More specifically, although some aspects of embodiments of the present invention may be identified herein as preferred or particularly advantageous, it is contemplated that the embodiments of the present invention are not limited to these preferred aspects.

Unless defined otherwise, all technical and scientific terms used herein have the same meaning as commonly understood by one of ordinary skill in the art to which the presently-disclosed subject matter belongs.

The presently disclosed data demonstrates that highly specific small molecule antagonists of the kinase domain of PFKFB4 suppress glucose metabolism and the proliferation of multiple cancer types. Importantly, such molecules reduce the glycolysis and intracellular F2,6BP of cancer cells, but do not inhibit recombinant PFK-1 or PFKFB3, which share the same substrate-binding domain and are also expressed in multiple cancer cell lines. Furthermore, the presently-disclosed data demonstrates that the cell cycle arrest effects of the small molecule antagonists of the kinase domain of PFKFB4 can be overcome by over-expression of PFKFB4, indicating that the anti cancer effects of such small molecule antagonists are due, at least in part, to their inhibition of PFKFB4. Because these small molecule antagonists of the kinase domain of PFKFB4 suppress glycolytic flux through the enolase reaction, the availability of both fructose 6-phosphate and glyceraldehyde 3-phosphate for ribose synthesis via the non-oxidative pentose shunt is reduced by these small molecule antagonists. Accordingly, the presently-disclosed data indicates that the observed G1 arrest in vitro caused by the presently-disclosed small molecule antagonists of the kinase domain of PFKFB4 (and by PFKFB4 siRNA) is a direct result of reduced availability of these glycolytic intermediates that are required for DNA synthesis during the S phase.

Molecular modeling was used to conduct virtual screens for novel ligands that might bind to the kinase as opposed to the bisphosphatase domain, due to the kinase activity being essential for neoplastic glucose metabolism and growth. The instant data demonstrates that the presently-disclosed small molecules are the first small molecule antagonists of PFKFB4 kinase activity. The presently-disclosed data demonstrates that said molecules not only reduce F2,6BP, but also glycolytic flux through PFK-1 and cell cycle progression into the S phase. The observation that pharmacological inhibition of the kinase domain of PFKFB4 suppresses cell proliferation thus provides "proof-of-concept" that PFKFB4 kinase inhibitors, as opposed to bisphosphatase inhibitors, may have utility as anti-cancer agents.

A related family member, PFKFB3, is encoded on a different chromosome and has a kinase:phosphatase ratio and tissue distribution distinct from PFKFB4. A series of small molecules have been developed that selectively inhibit PFKFB3. The relative roles of PFKFB3 and PFKFB4 are poorly understood. However, PFKFB4 appears to be essential for cancer cell survival and correlates highly with hypoxic regions of tumors, whereas PFKFB3 localizes to both the cytoplasm and the nucleus where it activates PFK-1 and cyclin dependent kinase 1 respectively. Surprisingly, the instant disclosure demonstrates that these two enzymes may provide some degree of reciprocal compensation and that dual inhibition of PFKFB3 and PFKFB4 may yield optimal suppression of intracellular F2,6BP and cell viability. In fact, studies conducted by the instant investigators have revealed that PFKFB4 expression is increased by PFKFB3 inhibition, suggesting that PFKFB4 may compensate for decreased PFKFB3 expression and activity and, importantly, may limit the efficacy of PFK15 (Tocris) and other PFKFB3 inhibitors. The instantly-disclosed data demonstrates that simultaneous administration of MPN-2 (determined by the instant investigators to be a PFKFB4 inhibitor) and PFK15 (Tocris, a commercially available PFKFB3 inhibitor) synergistically increases cell death in vitro. Thus, combination therapy with PFK15 (and other PFKFB3 inhibitors) and the presently-disclosed small molecule antagonists of the kinase domain of PFKFB4 may be used to provide an effective chemotherapeutic regimen.

Although there has been some degree of trepidation regarding the pharmacological targeting of enzymes that regulate an essential biochemical process such as glycolysis, the presently disclosed data demonstrate that PFKFB4, an enzyme expressed in several normal organs, can be pharmacologically inhibited without gross, histological, or laboratory signs of toxicity. Furthermore, the instant data demonstrate that the presently-disclosed small molecule inhibitors of the kinase domain of PFKFB4 were selectively cytostatic to RAS-transformed cells and not normal cells, and suppressed tumor growth without causing toxicity. This data is at least consistent with the hypothesis that neoplastic cells may be metabolically reprogrammed to rely more heavily on this regulator of metabolism. It is noteworthy that an inhibitor of the essential non-mutated cell cycle regulatory enzymes, CDK4 and CDK6, palbocicib, was recently found to double the progression-free survival of breast cancer patients without causing excessive toxicity. Based on this recent clinical success and the presently-disclosed data, PFKFB4 inhibitors that suppress glucose metabolism, such as the presently-disclosed small molecule antagonists of the kinase domain of PFKFB4, may yield favorable therapeutic indices in patients suffering with advanced solid cancers.

Accordingly, the presently-disclosed subject matter includes a method of treating cancer in a subject in need of treatment comprises administering to the subject an effective amount of a compound having the Formula (I):

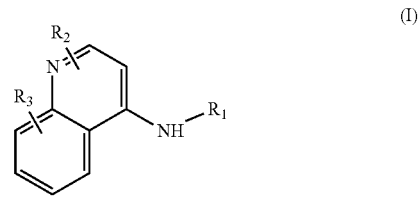

wherein:

$R_1$ is a $C_1$-$C_5$ alkyl nitrooxy;

$R_2$ can be present or absent, and when present is a $C_1$-$C_5$ alkyl;

$R_3$ can be present or absent, and when present is a $C_1$-$C_5$ alkoxy; and wherein if $R_2$ is present and located on the nitrogen of the quinoline group, said nitrogen has a positive charge.

In some embodiments, a method of treating cancer in a subject in need of treatment comprises administering to the subject an effective amount of a compound having the Formula (II):

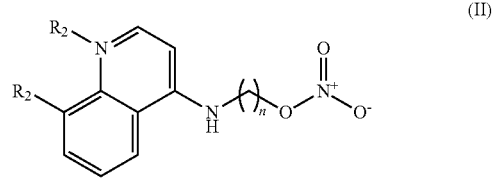

wherein:

n is 1-5;

R₁ can be present or absent, and when present is a $C_1$-$C_5$ alkoxy;

R₂ can be present or absent, and when present is a $C_1$-$C_5$ alkyl; and wherein if R₂ is present and located on the nitrogen of the quinoline group, said nitrogen has a positive charge.

In other embodiments, a method of treating cancer in a subject in need of treatment comprises administering to the subject an effective amount of a compound having the Formula (III):

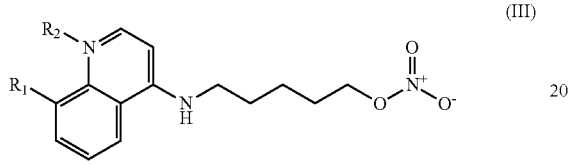
(III)

wherein:

R₁ can be present or absent, and when present is a $C_1$-$C_5$ alkoxy;

R₂ can be present or absent, and when present is a $C_1$-$C_5$ alkyl; and wherein if R₂ is present, the nitrogen of the quinoline group has a positive charge.

In further embodiments, a method of treating cancer in a subject in need of treatment thereof comprises administering to the subject an effective amount of a compound of:

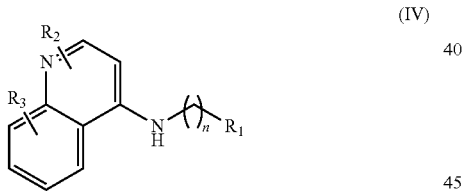
(IV)

wherein:

n is 1-6;

R₁ is carboxylic acid, methyl sulfonamide (-NH-SO₂-CH₃), carboxylic acid methyl ester, hydroxide, nitrate, or tert-butyl carbamate;

R₂ can be present or absent, and when present is a $C_1$-$C_5$ alkyl;

R₃ can be present or absent, and when present is a $C_1$-$C_5$ alkoxy, $C_1$-$C_5$ alkyl, chlorine, or hydrogen; and wherein if R₂ is present and located on the nitrogen of the quinoline group, said nitrogen has a positive charge. In other embodiments, R1 is a carbonate, a carbamide, nitro sulfonamide, or a thiocarbonyl. In certain embodiments, the compound of formula IV includes the compounds having the following formulae:

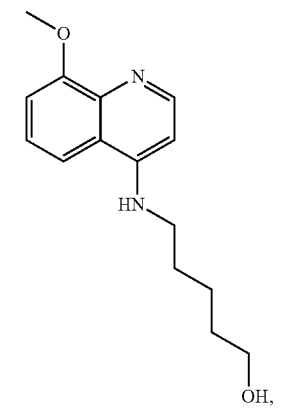

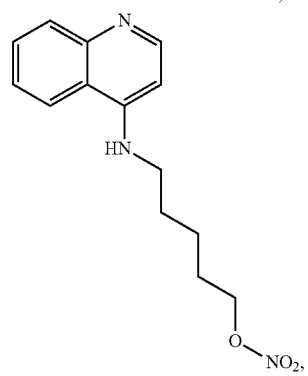

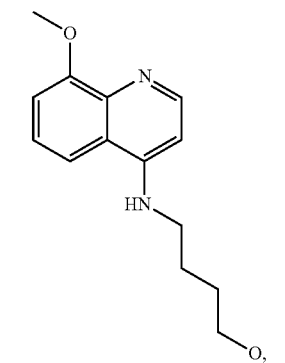

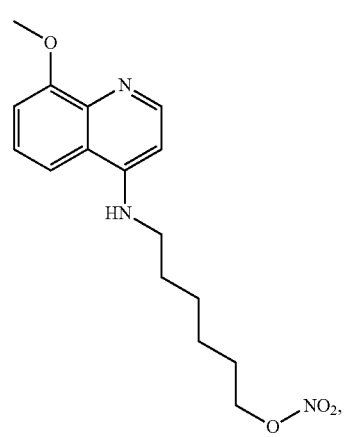

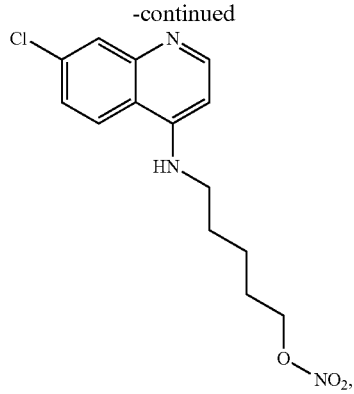

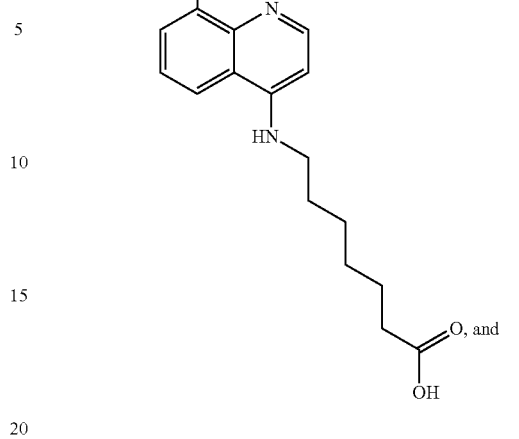

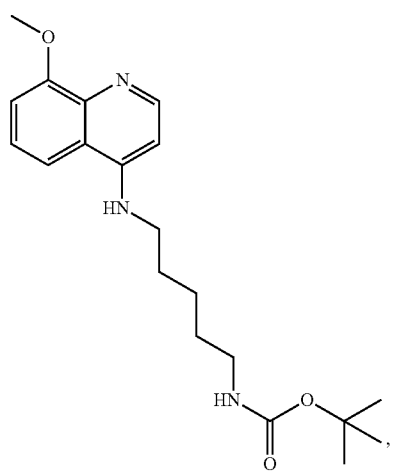

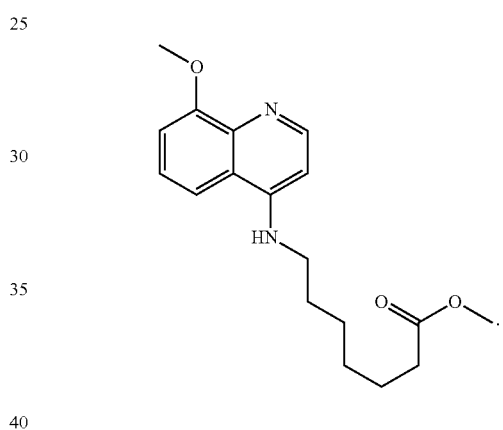

In other embodiments, a method of treating cancer in a subject in need of treatment thereof comprises administering to the subject an effective amount of a compound of:

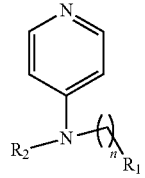

(V)

wherein:

n is 1-6;

$R_1$ nitrate; and $R_2$ is a hydrogen or nitrogen dioxide. In further embodiments, R1 is carboxylic acid, methyl sulfonamide (-NH-SO$_2$-CH$_3$), carboxylic acid methyl ester, hydroxide, nitrate, or tert-butyl carbamate. In even further embodiments, R1 is a carbonate, a carbamide, nitro sulfonamide, or a thiocarbonyl. In certain embodiments, the compound of formula V includes the compounds having the following formulae:

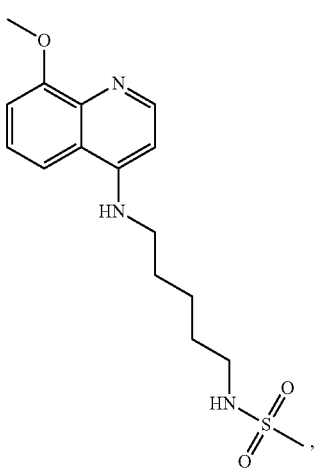 [SMILES: COc1cccc2c(NCCCCCNS(C)(=O)=O)ccnc12]

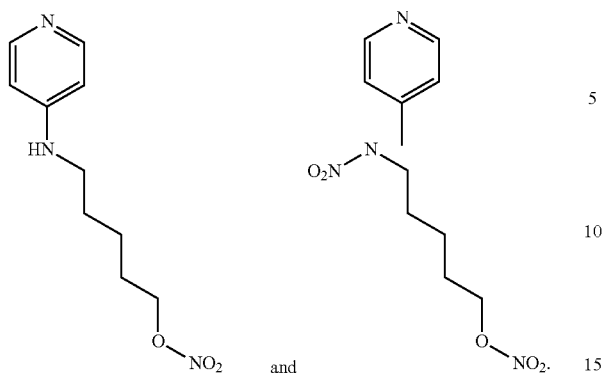

In additional embodiments, a method of treating cancer in a subject in need of treatment thereof comprises administering to the subject an effective amount of 5MPN.

In further embodiments, a method of treating cancer in a subject in need of treatment thereof comprises administering to the subject an effective amount of MPN-2.

In some embodiments, a method of treating cancer in a subject in need of treatment thereof comprises an effective amount of compound:

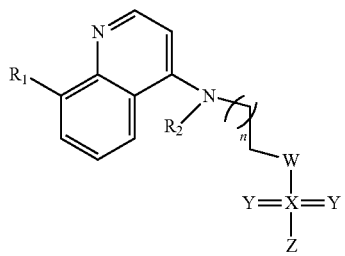

(VI)

wherein:

n is 2-6;

$R_1$ can be present or absent, and when present is a $C_1$-$C_5$ alkoxy, a $C_1$-$C_5$ alkyl, chlorine, or hydrogen;

$R_2$ can be present or absent, and when present is a hydrogen or nitrogen dioxide;

W is carbon, oxygen, nitrogen, hydrogen, methyl, methoxy, or hydroxide;

X can be present or absent, and when present is carbon, oxygen, nitrogen, or sulfer;

Y can be present or absent, and when present is oxygen, sulfer, or independently oxygen and sulfer and wherein one or two Ys may be present; and Z is can be present or absent, and when present is carbon, oxygen, nitrogen, hydrogen, methyl, or methoxy; and wherein if W is hydrogen, methyl, methoxy, or hydroxide, then X, Y, and Z is absent.

In some embodiments, a method of treating cancer in a subject in need of treatment thereof comprises an effective amount of compound:

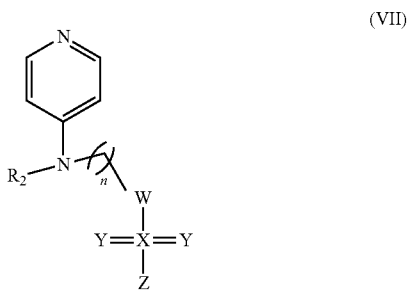

(VII)

wherein:

n is 1-6;

$R_2$ is a hydrogen or nitrogen dioxide;

W is carbon, oxygen, nitrogen, hydrogen, methyl, methoxy, or hydroxide;

X can be present or absent, and when present is carbon, oxygen, nitrogen, or sulfer;

Y can be present or absent, and when present is oxygen, sulfer, or independently oxygen and sulfer and wherein one or two Ys may be present; and Z is can be present or absent, and when present is carbon, oxygen, nitrogen, hydrogen, methyl, or methoxy; and wherein if W is hydrogen, methyl, methoxy, or hydroxide, then X, Y, and Z is absent.

"Cancer" refers to diseases caused by uncontrolled cell division and the ability of cells to metastasize, or to establish new growth in additional sites. It will be appreciated that the administration to a subject of an effective amount of the presently-disclosed small molecule antagonists of the kinase domain of PFKFB4 can provide therapy for a wide variety of cancers including, but not limited to solid tumors, such as lung, breast, colon, ovarian, brain, liver, pancreas, prostate, malignant melanoma, non-melanoma skin cancers, as well as hematologic tumors and/or malignancies, such as childhood leukemia and lymphomas, multiple myeloma, Hodgkin's disease, lymphomas of lymphocytic and cutaneous origin, acute and chronic leukemia such as acute lymphoblastic, acute myelocytic or chronic myelocytic leukemia, plasma cell neoplasm, lymphoid neoplasm and cancers associated with AIDS. In certain embodiments of a method of treating cancer in a subject in need of treatment thereof comprising administering to the subject an effective amount of the presently-disclosed small molecule antagonists of the kinase domain of PFKFB4 (including the compounds of Formulae (I), (II), and (III), (IV), (V), (VI), and (VII) as well as 5MPN or MPN-2), the cancer is selected from breast cancer, lung cancer, colon cancer, and prostate cancer.

As used herein, the term "treating" relates to any treatment of cancer, including but not limited to prophylactic treatment and therapeutic treatment. "Treating" includes any effect, e.g., lessening, reducing, modulating, or eliminating, that results in the improvement of the cancer. "Treating" or "treatment" of cancer state includes: inhibiting the cancer, i.e., arresting the development of the cancer or its clinical symptoms; or relieving the cancer, i.e., causing temporary or permanent regression of the cancer or its clinical symptoms.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In certain embodiments of a method of treating cancer in a subject in need of treatment thereof comprising administering to the subject an effective amount of the presently-disclosed small molecule antagonists of the kinase domain of PFKFB4 (including the compounds of Formulae (I), (II), and (III), (IV), (V), (VI), and (VII) as well as 5MPN or MPN-2), the subject that is administered an effective amount is a mammal.

An "effective amount" is defined herein in relation to the treatment of cancers is an amount that will decrease, reduce, inhibit, or otherwise abrogate the growth of a cancer cell or tumor. The "effective amount" will vary depending the cancer and its severity and the age, weight, etc., of the mammal to be treated.

It will be understood that the presently-disclosed small molecule antagonists of the kinase domain of PFKFB4 (including the compounds of Formulae (I), (II), and (III), (IV), (V), (VI), and (VII) as well as 5MPN or MPN-2), can include pharmaceutically acceptable salts, solvates, stereoisomers, and optical isomers thereof. It will further be understood that the compounds of Formulae (I), (II), and (ID), (IV), (V), (VI), and (VII), as well as 5MPN or MPN-2, can include prodrugs of such compounds.

"Pharmaceutically acceptable salt" of a compound means a salt that is pharmaceutically acceptable and that possesses the desired pharmacological activity of the parent compound. As used herein, "pharmaceutically acceptable salt" refers to derivative of the compounds of Formulae (I), (II), and (III), (IV), (V), (VI), and (VII) as well as 5MPN or MPN-2, wherein such compounds are modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycoloylarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

It should be understood that all references to the presently-disclosed small molecule antagonists of the kinase domain of PFKFB4 (including the compounds of Formulae (I), (II), and (III), (IV), (V), (VI), and (VII) as well as 5MPN or MPN-2), or pharmaceutically acceptable salts thereof, include solvent addition forms (solvates) or crystal forms (polymorphs) as defined herein.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

Additionally, the compounds of the present invention, for example, the salts of the presently-disclosed small molecule antagonists of the kinase domain of PFKFB4 (including the compounds of Formulae (I), (II), and (III), (IV), (V), (VI), and (VII) as well as 5MPN or MPN-2), can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non stoichiometric amounts of solvent. Some compounds or salts have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular slate as $H_2O$, such combination being able to form one or more hydrate.

The presently-disclosed small molecule antagonists of the kinase domain of PFKFB4 (including the compounds of Formulae (I), (II), and (III), (IV), (V), (VI), and (VII) as well as 5MPN or MPN-2) of the present invention can be prepared as prodrugs, for example pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.) The presently-disclosed small molecule antagonists of the kinase domain of PFKFB4 (including the compounds of Formulae (I), (II), and (III), (IV), (V), (VI), and (VII) as well as 5MPN or MPN-2) can be delivered in prodrug form. Thus, the present invention is intended to cover prodrugs of the presently-disclosed small molecule antagonists of the kinase domain of PFKFB4 (including the compounds of Formulae (I), (II), and (III), (IV), (V), (VI), and (VII) as well as 5MPN or MPN-2), methods of delivering the same and compositions containing the same. "Prodrugs" are intended to include any covalently bonded carriers that release an active parent drug of the present invention in vivo when such prodrug is administered to a subject.

In certain embodiments, the presently-disclosed small molecule antagonists of the kinase domain of PFKFB4 (including the compounds of Formulae (I), (II), and (III), (IV), (V), (VI), and (VII) as well as 5MPN or MPN-2) are administered at a dosage effective for specifically inhibiting 6-phosphofructo-2-kinase/fructose-2,6-bisphosphatase 4 (PFKFB4). In more specific embodiments, "specifically inhibiting" is defined as inhibiting PFKFB4 without inhibiting 6-phosphofructo-2-kinase/fructose-2,6,biphosphate 3 (PFKFB3), 6-phosphofructo-2-kinase/fructose-2,6-bisphosphatase 2 (PFKFB2), or 6-phosphofructo-2-kinase/fructose-2,6,biphosphate 1 (PFKFB1).

In some embodiments, the presently-disclosed small molecule antagonists of the kinase domain of PFKFB4 (including the compounds of Formulae (I), (II), and (111), (IV), (V), (VI), and (VII) as well as 5MPN or MPN-2) can be delivered regionally to a particular affected region or regions of the subject's body. In some embodiments, the presently-disclosed small molecule antagonists of the kinase domain of PFKFB4 (including the compounds of Formulae (I), (II), and (III), (IV), (V), (VI), and (VII) as well as 5MPN or MPN-2) can be administered systemically. For example, in some embodiments of a method treating cancer in a subject in need of treatment thereof, the presently-disclosed small molecule antagonists of the kinase domain of PFKFB4 (including the compounds of Formulae (I), (II), and (III), (IV), (V), (VI), and (VII) as well as 5MPN or MPN-2) are administered orally. In accordance with the presently disclosed methods, the presently-disclosed small molecule antagonists of the kinase domain of PFKFB4 (including the compounds of Formulae (I), (II), and (III), (IV), (V), (VI), and (VII) as well as 5MPN or MPN-2) can be administered orally as a solid or as a liquid. In other embodiments of treating cancer in a subject in need of treatment, the presently-disclosed small molecule antagonists of the kinase domain of PFKFB4 (including the compounds of Formulae (I), (II), and (III), (IV), (V), (VI), and (VII) as well as 5MPN or MPN-2) is administered intravenously. In accordance with the presently disclosed methods, the presently-disclosed small molecule antagonists of the kinase domain of PFKFB4 (including the compounds of Formulae (I), (II), and (III), (IV), (V), (VI), and (VII) as well as 5MPN or MPN-2) can be administered intravenously as a solution, suspension, or emulsion. Alternatively, the presently-disclosed small molecule antagonists of the kinase domain of PFKFB4 (including the compounds of Formulae (I), (IT), and (III), (VI), (V), (VI), and (VII) as well as 5MPN or MPN-2) also can be administered by inhalation, intravenously, or intramuscularly as a liposomal suspension.

In certain embodiments of a method of treating cancer in a subject in need of treatment thereof comprising administering to the subject an effective amount of the presently-disclosed small molecule antagonists of the kinase domain of PFKFB4 (including the compounds of Formulae (I), (II), and (III), (IV), (V), (VI), and (VII) as well as 5MPN or MPN-2), the subject that is administered an effective amount of said small molecule antagonist is substantially free of signs of toxicity. "Substantially free of signs of toxicity" includes unsafe deviations on complete blood counts, electrolytes, hepatic and renal function, body mass, and the unsafe deviations on the gross and histological appearance of the brain, heart, lungs, liver, kidneys, and spleen due to the administration of the presently-disclosed small molecule antagonists of the kinase domain of PFKFB4 (including the compounds of Formulae (I), (II), and (III), (IV), (V), (VI), and (VII) as well as 5MPN or MPN-22) to the subject.

In some embodiments of a method of treating cancer in a subject in need of treatment thereof comprising administering to the subject an effective amount of the presently-disclosed small molecule antagonists of the kinase domain of PFKFB4 (including the compounds of Formulae (I), (II), and (III), (IV), (V), (VI), and (VII) as well as 5MPN or MPN-2), the method further comprises administering to the subject one or more additional therapeutic compounds. It will be appreciated that therapeutic benefits for the treatment of cancer can be realized by combining treatment with the presently-disclosed small molecule antagonists of the kinase domain of PFKFB4 (including the compounds of Formulae (I), (II), and (III), (VI), (V), (VI), and (VII) as well as 5MPN or MPN-2) with one or more additional therapeutic compounds. The term "additional therapeutic compounds" includes anti-cancer agents or treatments. The choice of such combinations will depend on various factors including, but not limited to, the type of disease, the age and general health of the subject, the aggressiveness of disease progression, and the ability of the subject to tolerate the agents that comprise the combination. For example, the presently-disclosed small molecule antagonists of the kinase domain of PFKFB4 (including the compounds of Formulae (I), (IT), and (III), (IV), (V), (VI), and (VII) as well as 5MPN or MPN-2) can be combined with other agents and therapeutic regimens that are effective at reducing tumor size (e.g., radiation, surgery, chemotherapy, hormonal treatments, and, or gene therapy). Further, in some embodiments, it can be desirable to combine the presently-disclosed small molecule antagonists of the kinase domain of PFKFB4 (including the compounds of Formulae (I), (II), and (III), (IV), (V), (VI), and (VII) as well as 5MPN or MPN-2) with one or more agents that treat the side effects of a disease or the side effects of one of the additional therapeutic agents, e.g., providing the subject with an analgesic, or agents effective to stimulate the subject's own immune response (e.g., colony stimulating factor).

Thus, the term "additional therapeutic compounds" includes a variety of include anti-cancer agents or treatments, such as chemical compounds that are also known as anti-neoplastic agents or chemotherapeutic agents. The agents can be used in combination with the presently-disclosed small molecule antagonists of the kinase domain of PFKFB4 (including the compounds of Formulae (I), (II), and (III), (IV), (V), (VI), and (VII) as well as 5MPN or MPN-2). Such compounds include, but are not limited to, alkylating agents, DNA intercalators, protein synthesis inhibitors, inhibitors of DNA or RNA synthesis, DNA base analogs, topoisomerase inhibitors, anti-angiogenesis agents, and telomerase inhibitors or telomeric DNA binding compounds. For example, suitable alkylating agents include alkyl sulfonates, such as busulfan, improsulfan, and piposulfan; aziridines, such as a benzodizepa, carboquone, meturedepa, and uredepa; ethylenimines and methylmelamines, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; nitroso ureas, such as carmustine, chlorozotocin, fotemustine, lomustine, nimustine, and ranimustine.

Antibiotics used in the treatment of cancer and that can be combined with the presently-disclosed small molecule antagonists of the kinase domain of PFKFB4 (including the compounds of Formulae (I), (II), and (in), (IV), (V), (VI), and (VII) as well as 5MPN or MPN-2) include dactinomycin, daunorubicin, doxorubicin, idarubicin, bleomycin sulfate, mytomycin, plicamycin, and streptozocin. Chemotherapeutic antimetabolites can also be combined with the presently-disclosed small molecule antagonists of the kinase domain of PFKFB4 (including the compounds of Formulae (I), (II), and (III), (IV), (V), (VI), and (VII) as well as 5MPN or MPN-2) for the treatment of cancer, and include mercaptopurine, thioguanine, cladribine, fludarabine phosphate, fluorouracil (5-FU), floxuridine, cytarabine, pentostatin, methotrexate, and azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxonorleucine, dideoxynucleosides, 5-fluorodeoxycytidine, 5-fluorodeoxyuridine, and hydroxyurea.

Chemotherapeutic protein synthesis inhibitors can also be combined with the presently-disclosed small molecule antagonists of the kinase domain of PFKFB4 (including the compounds of Formulae (I), (II), and (III), (IV), (V), (VI), and (VII) as well as 5MPN or MPN-2) for the treatment of cancer. Such inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine.

Additionally, protein synthesis inhibitors can also be combined with the presently-disclosed small molecule antagonists of the kinase domain of PFKFB4 (including the compounds of Formulae (I), (II), and (III), (IV), (V), (VI), and (VII) as well as 5MPN or MPN-2) for the treatment of cancer. Such inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim. Furthermore, inhibitors of DNA synthesis can be combined with the presently-disclosed small molecule antagonists of the kinase domain of PFKFB4 (including the compounds of Formulae (I), (II), and (III), (IV), (V), (VI), and (VII) as well as 5MPN or MPN-2) for the treatment of cancer. Such inhibitors include alkylating agents such as dimethyl sulfate, mitomycin C, nitrogen and sulfur mustards, intercalating agents, such as acridine dyes, actinomycins, adriamycin, anthracenes, benzopyrene, ethidium bromide, propidium diiodide-intertwining, and agents, such as distamycin and netropsin. Topoisomerase inhibitors, such as coumermycin, nalidixic acid, novobiocin, and oxolinic acid, inhibitors of cell division, including colcemide, colchicine, vinblastine, and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin, and streptolydigin also can be combined with the presently-disclosed small molecule antagonists of the kinase domain of PFKFB4 (including the compounds of Formulae (I), (II), and (III), (IV), (V), (VI), and (VII) as well as 5MPN or MPN-2) to provide a suitable cancer treatment.

Thus, current chemotherapeutic agents that can be used in a combination treatment with the presently-disclosed small molecule antagonists of the kinase domain of PFKFB4 (including the compounds of Formulae (I), (II), and (III), (IV), (V), (VI), and (VII) as well as 5MPN or MPN-2) include, but are not limited to, adrimycin, 5-fluorouracil (5FU), etoposide, camptothecin, actinomycin-D, mitomycin, cisplatin, hydrogen peroxide, carboplatin, procarbazine, mechlorethamine, cyclophosphamide, ifosfamide, melphalan, chlorambucil, bisulfan, nitrosurea, dactinomycin, duanorubicin, doxorubicin, bleomycin, plicomycin, tamoxifen, taxol, transplatimun, vinblastin, and methotrexate, and the like.

"Additional therapeutic compounds" can further involve immunotherapy directed at tumor antigen markers that are found on the surface of tumor cells. Treatment of a cancer with the presently-disclosed small molecule antagonists of the kinase domain of PFKFB4 (including the compounds of Formulae (I), (II), and (III), (IV), (V), (VI), and (VII) as well as 5MPN or MPN-2) can further be combined with a gene therapy based treatment, targeted towards oncogenes and/or cell cycle controlling genes, such as p53, p16, p21, Rb, APC, DCC, NF-1, NF-2, BRCA2, FHIT, WT-1, MEN-I, MEN U, BRCA1. VHL, FCC, MCC, ras, myc, neu, raf, erb, src, fms, jun, irk, ret, gsp, hst, bcl, and abl, which are often mutated versions of their normal cellular counterparts in cancerous tissues.

In more specific embodiments of a method of treating cancer in a subject in need of treatment thereof comprising administering to the subject an effective amount of the presently-disclosed small molecule antagonists of the kinase domain of PFKFB4 (including the compounds of Formulae (I), (II), and (III), (VI), (V), (VI), and (VII) as well as 5MPN or MPN-2), one or more additional therapeutic compounds comprise one or more of a PFKFB3 inhibitor, a PFKFB2 inhibitor, and a PFKFB1 inhibitor. In certain embodiments, the one or more PFKFB3 inhibitor is PFK15.

The additional therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

Additional cancer treatments can be used in combination with administration of the presently-disclosed small molecule antagonists of the kinase domain of PFKFB4 (including the compounds of Formulae (I), (II), and (III), (VI), (V), (VI), and (VII) as well as 5MPN or MPN-2). For example, the presently-disclosed small molecule antagonists of the kinase domain of PFKFB4 (including the compounds of Formulae (I), (II), and (III), (VI), (V), (VI), and (VII) as well as 5MPN or MPN-2) can be used as part of a treatment course further involving attempts to surgically remove part or all of a cancerous growth. For instance, the presently-disclosed small molecule antagonists of tire kinase domain of PFKFB4 (including the compounds of Formulae (I), (II), and (III), (IV), (V), (VI), and (VII) as well as 5MPN or MPN-2) can be administered after surgical treatment of a subject to treat any remaining neoplastic or metastasized cells. Treatment with the presently-disclosed small molecule antagonists of the kinase domain of PFKFB4 (including the compounds of Formulae (I), (II), and (III), (IV), (V), (VI), and (VII) as well as 5MPN or MPN-2) can also precede surgery, in an effort to shrink the size of a tumor to reduce the amount of tissue to be excised, thereby making the surgery less invasive and traumatic. Furthermore, treatment with the presently-disclosed small molecule antagonists of the kinase domain of PFKFB4 (including the compounds of Formulae (I), (II), and (III), (IV), (V), (VI), and (VII) as well as 5MPN or MPN-2) can include one or more treatment courses with a radiotherapeutic agent to induce DNA damage. Radiotherapeutic agents, include, for example, gamma irradiation, X-rays. UV-irradiation, microwaves, electronic emissions, radioisotopes, and the like. Therapy can be achieved by irradiating the localized tumor site with the above-described forms of radiation.

In other embodiments of the presently-disclosed subject matter, a pharmaceutical composition comprising an effective amount of the presently-disclosed small molecule antagonists of the kinase domain of PFKFB4 (including the compounds of Formulae (I), (II), and (III), (IV), (V), (VI), and (VII) as well as 5MPN or MPN-2) and at least one pharmaceutical excipient is provided. "Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Thus, the term "pharmaceutical excipient" is used herein to describe any ingredient other than the compound(s) of the invention. Examples of pharmaceutical excipients include one or more substances which may act as diluents, flavoring agents, solubilisers, lubricants, suspending agents, binders, preservatives, wetting agents, tablet disintegrating agents, or an encapsulating material. The choice of excipient will to a large extent depend on factors such as the particular mode of administration, the effect of the excipient on solubility and stability, and the nature of the dosage form. A "pharmaceutical excipient" includes both one and more than one such excipient.

In certain embodiments of a pharmaceutical composition comprising an effective amount of the presently-disclosed small molecule antagonists of the kinase domain of PFKFB4 (including the compounds of Formulae (I), (II), and (III), (IV), (V), (VI), and (VII) as well as 5MPN or MPN-2) and at least one pharmaceutical excipient, the presently-disclosed small molecule antagonists of the kinase domain of PFKFB4 (including the compounds of Formulae (I), (II), and (III), (IV), (V), (VI), and (VII) as well as 5MPN or MPN-2) is an amount that specifically inhibits PFKFB4. Thus, in embodiments of the pharmaceutical composition, the presently-disclosed small molecule antagonists of the kinase domain of PFKFB4 are specific inhibitors of the activity of PFKFB4. In some aspects, the specific inhibitors of PFKFB4 inhibits the activity of PFKFB4 by at least about 25%, 30%, 35%, 40%, 45%, 50%, 55%, 60%, 65%, 70%. 75%, 80%, 85%, 90%, 95% 99%, or any value or range in between, but does not inhibit the activity of PFKFB1, PFKFB2, PFKFB3 by more than about 20%, 15%, 10%, 5%, 2%, or 1%.

The pharmaceutical composition comprising an effective amount of the presently-disclosed small molecule antagonists of the kinase domain of PFKFB4 (including the compounds of Formulae (I), (II), and (III), (IV), (V), (VI), and (VII) as well as 5MPN or MPN-2) and at least one pharmaceutical excipient described herein can be formulated with a pharmaceutically acceptable carrier for administration to a human or an animal. As such, the pharmaceutical compositions can be administered orally as a solid or as a liquid, or can be administered intramuscularly or intravenously as a solution, suspension, or emulsion. Alternatively, the pharmaceutical compositions can be administered by inhalation, intravenously, or intramuscularly as a liposomal suspension. In some embodiments, the pharmaceutical composition is formulated for oral administration. In other embodiments, the pharmaceutical composition is formulated for intravenous administration.

In some embodiments of a pharmaceutical composition comprising an effective amount of the presently-disclosed small molecule antagonists of the kinase domain of PFKFB4 (including the compounds of Formulae (I), (II), and (III), (IV), (V), (VI), and (VII) as well as 5MPN or MPN-2) and at least one pharmaceutical excipient, the pharmaceutical composition comprises one or more additional therapeutic agents, as defined above. In certain embodiments, the one or more additional therapeutic compounds comprise one or more of a PFKFB3 inhibitor, a PFKFB2 inhibitor, and a PFKFB1 inhibitor.

In other embodiments of the presently-disclosed subject matter, a method of inhibiting PFKFB4 in a cell comprising contacting the cell with an effective amount of the presently-disclosed small molecule antagonists of the kinase domain of PFKFB4 (including the compounds of Formulae (I), (II), and (III), (VI), (V), (VI), and (VII) as well as 5MPN or MPN-2) is provided. In certain embodiments, PFKFB4 is specifically inhibited by the presently-disclosed small molecule antagonists of the kinase domain of PFKFB4. Thus, in certain embodiments, the presently-disclosed small molecule antagonists of the kinase domain of PFKFB4 are specific inhibitors of the activity of PFKFB4. In some aspects, the specific inhibitors of PFKFB4 inhibits the activity of PFKFB4 by at least about 25%, 30%, 35%, 40%, 45%, 50%, 55%, 60%, 65%, 70%, 75%, 80%, 85%, 90%, 95% 99%, or any value or range in between, but does not inhibit the activity of PFKFB1, PFKFB2, PFKFB3 by more than about 20%, 15%, 10%, 5%, 2%, or 1%.

In some embodiments of a method of inhibiting PFKFB4 in a cell comprising contacting the cell with an effective amount of the presently-disclosed small molecule antagonists of the kinase domain of PFKFB4 (including the compounds of Formulae (I), (II), and (III), (VI), (V), (VI), and (VII) as well as 5MPN or MPN-2), the cell is a mammalian cell. In certain embodiments, the cell is a cancer cell. In other embodiments, the cell is derived from a cell line comprising H460, H1299, H441, H522. A549, MDA-MB-231, LNCaP, HCT116, or LLC cell lines.

In other embodiments of the presently-disclosed subject matter, a method of inhibiting PFKFB4 in a subject in need thereof comprising administering to the subject an effective amount of the presently-disclosed small molecule antagonists of the kinase domain of PFKFB4 (including the compounds of Formulae (I), (II), and (III), (IV), (V), (VI), and (VII) as well as 5MPN or MPN-2) is provided. In certain embodiments, the presently-disclosed small molecule antagonists of the kinase domain of PFKFB4 (including the compounds of Formulae (I), (II), and (111), (IV), (V), (VI), and (VII) as well as 5MPN or MPN-2) is administered at a dosage effective for specifically inhibiting PFKFB4. In some aspects, the specific inhibitors of PFKFB4 inhibits the activity of PFKFB4 by at least about 25%, 30%, 35%, 40%, 45%, 50%, 55%, 60%, 65%, 70%. 75%, 80%, 85%, 90%, 95% 99%, or any value or range in between, but does not inhibit the activity of PFKFB1, PFKFB2, PFKFB3 by more than about 20%, 15%, 10%, 5%, 2%, or 1%.

In some embodiments of a method of inhibiting PFKFB4 in a subject in need thereof comprising administering to the subject an effective amount of the presently-disclosed small molecule antagonists of the kinase domain of PFKFB4 (including the compounds of Formulae (I), (II), and (III), as well as 5MPN or MPN-2), with said small molecule antagonists administered orally. In other embodiments, the presently-disclosed small molecule antagonists of the kinase domain of PFKFB4 (including the compounds of Formulae (I), (II), and (III), (IV), (V), (VI), and (VII) as well as 5MPN or MPN-2) are administered intravenously.

In some embodiments of a method of inhibiting PFKFB4 in a subject comprising administering to the subject an effective amount of the presently-disclosed small molecule antagonists of the kinase domain of PFKFB4 (including the compounds of Formulae (I), (II), and (III), (IV), (V), (VI), and (VII) as well as 5MPN or MPN-2), the subject remains substantially free of signs of toxicity.

In other embodiments of the presently-disclosed subject matter, a method of reducing proliferative capacity of a cell comprising contacting the cell with an effective amount of the presently-disclosed small molecule antagonists of the kinase domain of PFKFB4 (including the compounds of Formulae (I), (II), and (III), (IV), (V), (VI), and (VII) as well as 5MPN or MPN-2) is provided. In certain embodiments, the cell is contacted with the presently-disclosed small molecule antagonists of the kinase domain of PFKFB4 (including the compounds of Formulae (I), (II), and (III), (IV), (V), (VI), and (VII) as well as 5MPN or MPN-2) at a dosage effective for specifically inhibiting PFKFB4. In some aspects, the specific inhibitors of PFKFB4 inhibits the activity of PFKFB4 by at least about 25%, 30%, 35%, 40%, 45%, 50%, 55%, 60%, 65%, 70%. 75%, 80%, 85%, 90%, 95% 99%, or any value or range in between, but does not inhibit the activity of PFKFB1, PFKFB2, PFKFB3 by more than about 20%, 15%, 10%, 5%, 2%, or 1%.

In some embodiments of a method of method of reducing proliferative capacity of a cell comprising contacting the cell with an effective amount of the presently-disclosed small molecule antagonists of the kinase domain of PFKFB4 (including the compounds of Formulae (I), (II), and (III), (IV), (V), (VI), and (VII) as well as 5MPN or MPN-2), the cell is a mammalian cell. In certain embodiments, the cell is a cancer cell. In other embodiments, the cell is derived from a cell line comprising H460, H1299. H441, H522, A549, MDA-MB-231, LNCaP, HCT116, or LLC cell lines.

In other embodiments of the presently-disclosed subject matter, a method of reducing fructose-2,6-bisphosphate (F2,6BP) in a cell comprising contacting the cell with an effective amount of the presently-disclosed small molecule antagonists of the kinase domain of PFKFB4 (including the compounds of Formulae (I), (II), and (III), (IV), (V), (VI), and (VII) as well as 5MPN or MPN-2) is provided. In some embodiments, the cell is a mammalian cell. In certain embodiments, the cell is a cancer cell.

EXAMPLES

The following examples are given by way of illustration and are in no way intended to limit the scope of the present invention.

Example 1

Material and Methods

Cell lines and cell culture: H460, H1299, H441, H522 and A549 non-small cell lung cancer (NSCLC), MDA-MB-231 (breast), LNCaP (prostatic) and HCT116 (colon) adenocarcinoma and Lewis lung carcinoma (LLC) cell lines were obtained from ATCC and used within 6 months of acquisition, PFKFB4$^7$ ear pinna Fibroblasts isolated from TamCre/loxP/PFKFB4$^{-/-}$ mice were immortalized as described previously (Chesney J et al. Fructose-2,6-bisphosphate synthesis by 6-phosphofructo-2-kinase/fructose-2,6-bisphosphatase 4 (PFKFB4) is required for the glycolytic response to hypoxia and tumor growth. Oncotarget 2014 Aug. 30; 5(16):6670-86). Normal bronchial epithelial cells (NHBE) were obtained from Lonza and NHBE cells expressing telomerase, SV40 large T antigen and activated Ras (hT/LT/Ras) were a gift from Dr. B. J. Rollins, Dana Farber Cancer Institute. All cell lines were tested and found negative for mycoplasma (PCR Mycoplasma Detection Kit, ABM). Cell lines were grown in DMEM (A549, LNCaP, MDA-MB-231, LLC and PFKFB4$^{-/-}$), RPMI 1640 (H460, H1299, H441, H522) and McCoy's 5A media (HCT116) (all from Invitrogen) containing 10% fetal calf serum (Hyclone). NHBE and hT/LT/Ras cells were grown in BEGM containing SingleQuots (Lonza). All lines were cultured at 37° C. in 5% $CO_2$. In certain experiments, 4-hydroxytamoxifen (4HT, Sigma-Aldrich) was added to PFKFB4$^{-/-}$ fibroblasts at indicated concentrations.

Cell Viability: Cells were incubated in 20% trypan blue (Sigma) for 5 minutes. Cells excluding trypan blue were counted using a standard hemocytometer (Hausser Scientific) to determine total numbers of viable cells. Data are expressed as mean±SD of three experiments.

PFKFB4 Modeling and Compound Screen: The PFKFB4 homology model used the rat testes PFKFB4 isozyme X-ray structure (PDB code 1BIF) as a structural template. An alignment was generated using Clustal W (Chenna R el al. Multiple sequence alignment with the Clustal series of programs. Nucleic Acids Res 2003 Jul. 1; 31(13):3497-500). Four homology models were generated using Modeller (Sali A. Blundell T L. Comparative protein modeling by satisfaction of spatial restraints. J Mol Biol 1993 Dec. 5; 234 (3):779-815), and the structure that best reproduced the PFKFB4 binding site selected for further use. The residues essential to ligand binding and protein activity for PFKFB4 were correlated to equivalent residue numbers in the consensus structure. The catalytic site residues were selected to produce a residue-based protomol for Surflex 1.33 (Jain A N. Surflex: fully automatic flexible molecular docking using a molecular similarity-based search engine. J Med Chem 2003 Feb. 13:46(4):499-511) for the virtual screening run using the 2007 ZINC-drug-like library containing 3,381,225 compounds. The highest-scoring 100 molecules were identified for purchase. All computational work, and virtual screening was done in the Brown Cancer Center Molecular Modeling Facility. The top 30 commercially available compounds were purchased and examined for inhibitory effects on H460 cell proliferation and recombinant PFKFB4 activity.

Transfections: For siRNA experiments, cells growing in 6-well plates were transfected with control (Stealth Negative Control Medium GC, Invitrogen) or PFKFB4 siRNA (siFB4, HSS107863, Invitrogen) using Lipofectamine RNAiMax (Invitrogen) and harvested as indicated. For overexpression experiments, cells were transfected with pCMV-XL4 (vector) or pCMV-XL4 containing full-length PFKFB4 (Origene) using Lipofectamine 2000 (Invitrogen) and harvested as indicated.

Protein extraction and Western blotting: Protein extraction and blotting were conducted as previously described. Membranes were probed with antibodies to PFKFB4 (Abeam) or β-actin (Sigma) followed by HRP-conjugated goat anti-rabbit or anti-mouse secondary antibodies respectively (Pierce). Data shown are representative of three experiments.

Kinase assays: The fructose-6-phosphate kinase activity of human recombinant PFKFB4 in the presence of DMSO±indicated 5MPN concentrations was assayed as previously described. The activity of 5MPN against 97 kinases was examined using a commercially available active-site dependent competition binding assay core service (KINOMEscanEDGE) that quantifies the capacity of lest agents to compete with an immobilized, active-site directed ligand using a DNA-tagged kinase and immobilized ligand and compound. For example, enzyme inhibition was studies using a ADP-Glo assay. The effect of MPN-2 on the activity of recombinant human PFKFB4 enzyme was examined in an ADP-Glo assay (Promega), which measures ADP formed from a kinase reaction. ADP is converted into ATP, which is converted into light by a luciferase. PFKFB4 protein was exposed to MPN-2 at indicated concentrations in the presence of ATP and fructose-6-phosphate and following manufacturer's instructions, ADP-Glo and kinase detections reagents were added. The data are shown as the decrease in luminescence caused by MPN-2 relative to DMSO.

F2,6BP measurements: Cells or tissues were prepared as previously described and F2,6BP content measured using a coupled enzyme reaction following the method of Van Schaftingen et at (Van Schaftingen E et al. A kinetic study of pyrophosphate: fructose-6-phosphate phosphotransferase from potato tubers. Application to a microassay of fructose 2,6-bisphosphate. Eur J Biochem 1982 December; 129(1): 191-5) and normalized to total cellular protein measured by the bicinchoninic acid assay (BCA, Thermo Scientific). For example, H460 cells were exposed to the indicated concentrations of MPN-2. In order to measure F2,6BP, cells were harvested, washed with PBS, lysed in NaOH/Tris acetate by heating at 80° C. and lysates neutralized to pH 7.2. F2,6BP content was measured using a coupled enzyme reaction following the method of Van Schaftingen et al (Eur J Biochem. 1982; 129(1): 191-195). The F2,6BP concentration was normalized to total cellular protein measured by the bicinchoninic acid assay (BCA, Thermo Scientific) All data are expressed as the mean±SD of three experiments. Statistical significance was assessed by the two-sample t test (independent variable).

Glycolysis Assay: H460 cells were exposed to the indicated concentrations of MPN-2 and glycolysis production was examined. Cells growing in 6-well plates were incubated in 500 µl of complete medium containing 1 µCi of 5-[$^3$H]glucose per well for 60 min in 5% $CO_2$ at 37° C. Media was collected, $^3H_2O$ formed via glycolysis from the 5-[$^3$H]glucose measured and counts normalized as previously described. For example, the medium was then collected and centrifuged to pellet any suspended cells. To separate the $^3H_2O$ formed via glycolysis from the 5-[$^3$H] glucose added to the medium, an evaporation technique in a sealed system was utilized. Briefly, 150 µl aliquots of medium were added to open tubes that were placed upright inside scintillation vials containing 1 ml of $H_2O$. The scintillation vials were sealed, and the $^3H_2O$ produced by glycolysis through enolase and released to the medium was allowed to equilibrate with the $H_2O$ in the outer vial for 48 h at 37° C. The amounts of $^3H_2O$ that had diffused into the surrounding $H_2O$ was measured on a Tri-Carb 2910 liquid scintillation analyzer (Perkin Elmer) and compared with $^3H_2O$ and 5-[$^3$H]glucose standards. Protein concentration was determined using the BCA assay and counts were normalized to protein concentration. All data are expressed as the mean±SD of three experiments. Statistical significance was assessed by the two-sample t test (independent variable).

ATP Measurements: H460 cells were exposed to the indicated concentrations of MPN-2 and ATP production was examined. Cells were lysed and intracellular ATP determined as described previously. For example, cells were washed (while still adherent) with cold PBS 1×, lysed with Passive Lysis Buffer (1×; Molecular Probes, Invitrogen) added directly to the plates, and immediately harvested by scraping. The lysates were flash frozen (to −80° C.) and thawed (to 37° C.) once to accomplish complete lysis and then centrifuged (at 4° C.) for 30 seconds to clear the lysates. Intracellular ATP levels were determined using a bioluminescence assay (Molecular Probes), utilizing recombinant firefly luciferase and its substrate, D-luciferin. The luminescence was read in a TD-20/20 luminometer (Turner Designs) at 560 nm. The ATP values were calculated using an ATP standard curve. The protein concentrations of the lysates were estimated using the BCA assay (Pierce Biotechnology) and ATP was expressed as pmol/µg protein. All data are expressed as the mean±SD of three experiments. Statistical significance was assessed by the two-sample t test (independent variable).

Proliferation Assays: H460 non-small cell lung cancer cells were plated in 24 well plates and exposed to increasing concentrations of the indicated inhibitors of Formula IV (FBR1-02 corresponds to

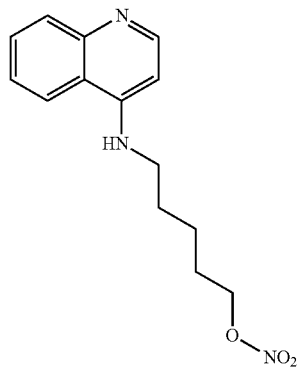 [SMILES: O=[N+]([O-])OCCCCCNc1ccnc2ccccc12]

and FBR1-09 corresponds to

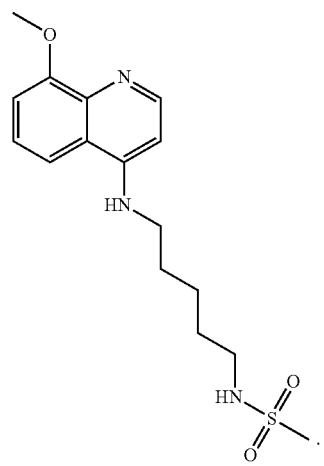 [SMILES: COc1cccc2c(NCCCCCNS(C)(=O)=O)ccnc12]

DMSO was used as vehicle. After 24, 48 and 72 hours of exposure, cells were detached and viable cells were counted by Trypan blue exclusion (representative counts at 48 hours shown).

Flow Cytometry: To measure apoptosis, cells were stained with annexin V and propidium iodide and examined as previously described. For example, H460 cells were exposed to increasing concentrations of the PFKFB4 inhibitor (MPN-2), the PFKFB3 inhibitor PFK15 (Tocris) or both and viable cells were counted at 24, 48 and 72 hours. DMSO used as vehicle. For cell cycle experiments, cells were detached, washed with cold PBS and fixed in 70% ethanol (4° C. 30 minutes). The cells then were pelleted by centrifugation, resuspended in PBS containing PI and RNase A, incubated at 37° C. in the dark for 30 minutes and analyzed by flow cytometry (BD FACSCalibur). Data were analyzed using FlowJo software (TREE STAR Inc.). Results were calculated as the mean±SD of three experiments. The effects (Fa values) of the series of concentrations of MPN-2 and PFK-15 were examined individually and in combination at a constant ratio of 1:1. From these data, the CI values at various Fa levels were calculated (using the CompuSyn program and the CI algorithm, from Chou and Martin) and are also represented as a Combination Index plot and an isobologram for the combination of MPN-2 and PFK15. The CI values are <1 indicating that the combination of MPN-2 and PFK15 is synergistic (also seen in both plots by location of the data points below the lines that indicate additive effects).

In vivo Studies. The pharmacokinetic profile was determined in female C57BL/6 mice following IV and oral administration of 5MPN. Using only female mice lowered the animal numbers required for meaningful results without issues of potential gender differences in exposure. Eight time points (n=3/time point) were used to determine PK parameters calculated using WinNonLin v5.0. Plasma samples were extracted using acetonitrile and analyzed by LC/MS-MS using a PhenomexSynergi Polar-RP 4 micron 50×2.0 mm column eluted with a biphasic mobile phase (0.5% formic acid in acetonitrile and water).

For xenograft studies, exponentially growing LLC or H460 cells were detached, washed and resuspended in PBS. Female C57BL/6 mice (Jackson Labs) were injected with LLC cells (n=10/group, s.c., 1×10$^6$ cells) and female BALB/c athymic mice (Jackson Labs) with H460 cells (n=10/group, s.c, 5×10$^6$ cells). Tumor masses were determined in a blinded fashion with Vernier calipers using the formula: mass (mg)=(width, mm)$^2$×(length, mm)/2 as previously described. When tumor masses were 150-200 mg, mice were randomized to daily intraperitoneal DMSO or 5MPN at the indicated dose in 50 µL DMSO. Tumor measurements and body weights were followed daily. All data are expressed as the mean±SD of two experiments. Statistical significance was assessed by the two-sample t test (independent variable).

At the end of the experiment, animals were euthanized, tumors removed and sections fixed in 10% formaldehyde for immunohistochemistry or snap-frozen in liquid nitrogen for analyses. Subsets of tumor-bearing mice (n=3) were injected i.p. with 2-[$^{18}$F]-fluoro-2-deoxyglucose (FDG, 150 µCi, 100 µl) and imaged by micro-positron emission tomography as previously described. Regions of interest in the tumors and cerebellum were quantified in quadruplicate and expressed as the mean±SD of the tumor:cerebellar FDG uptake ratio. Animal experiments were approved by the University of Louisville Institutional Animal Care and Use Committee.

Immunohistochemistry: Formalin-fixed, paraffin-embedded tissue sections were processed as previously described then incubated with anti-Ki-67 primary antibody (Abeam) overnight, followed by HRP-linked goat anti-rabbit secondary antibody (1:300. Pierce). Sections were developed with 3,3'-diaminobenzidine tetrahydrochloride, counterstained, scanned and analyzed with the positive pixel count algorithm as previously described. Data are depicted as % positive pixels/total pixels±SD.

Example 2

Small Molecule Antagonists of PFKFB4

Figure 1:
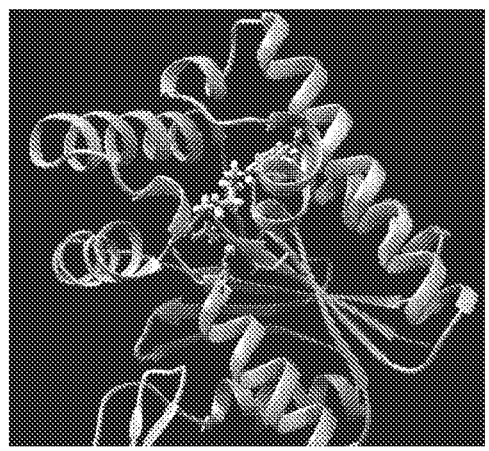
FIG. 1. Compound 5MPN inhibits recombinant PFKFB4 enzyme activity.
Figure 1:
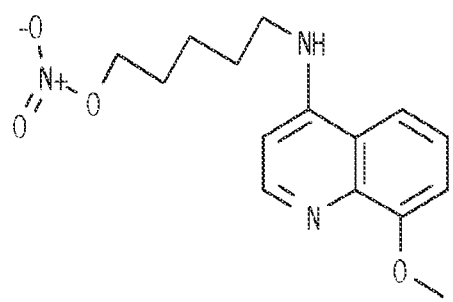
Figure 1:
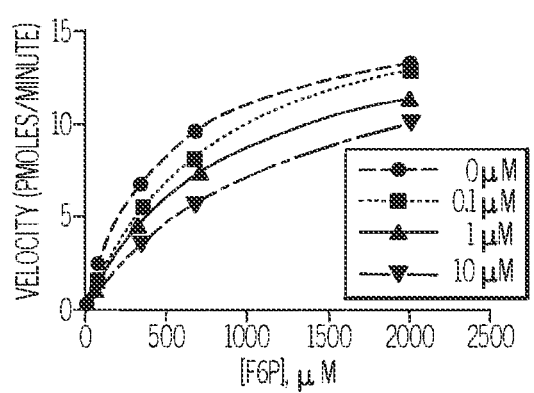
Figure 1:
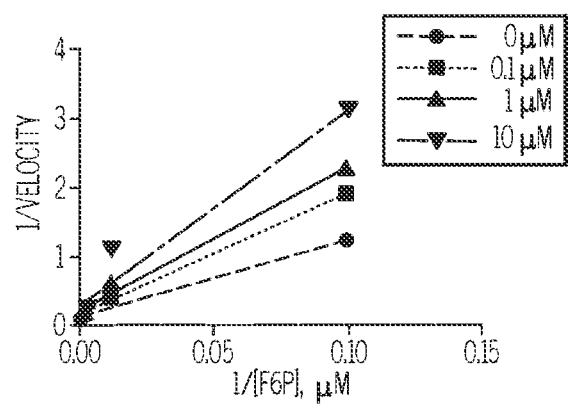

Results: We utilized the X-ray structure of the *Ratus norvegicus* testes PFKFB4 (Hasemann C A et al. The crystal structure of the bifunctional enzyme 6-phosphofructo-2-kinase/fructose-2,6-bisphosphatase reveals distinct domain homologies. Structure 1996 Sep. 15; 4(9): 1017-29.) to conduct an in silico screen of >18 million small molecules to identify potential compounds that may interact with the fructose 6-phosphate (F6P) binding domain of PFKFB4. Over one hundred compounds were identified, scored, ranked, and analyzed based on their association potential with the active site within PFKFB4. We physically tested the 30 best-score compounds for their ability to inhibit the kinase activity of recombinant PFKFB4. For example, 5-[(8-methoxyquinolin-4-yl)amino]pentyl nitrate (termed 5MPN; FIG. 1A and FIG. 1B), significantly inhibited PFKFB4 activity (FIG. 1C). Based on Lineweaver-Burk analyses, this compound appears to be a competitive inhibitor of the F6P binding site (FIG. 1D). Importantly, this compound did not inhibit PFK-1 or PFKFB3 which share the identical substrate and are co-expressed with PFKFB4 in multiple cell lines and required for glucose metabolism (no inhibition of kinase activity with 10 µM). Additionally, a panel of 97 protein kinases was not inhibited by 10 µM of 5MPN providing further support for the selectivity of this compound for PFKFB4 (KINOMEscan, data not shown).

Example 3

Figure 2:
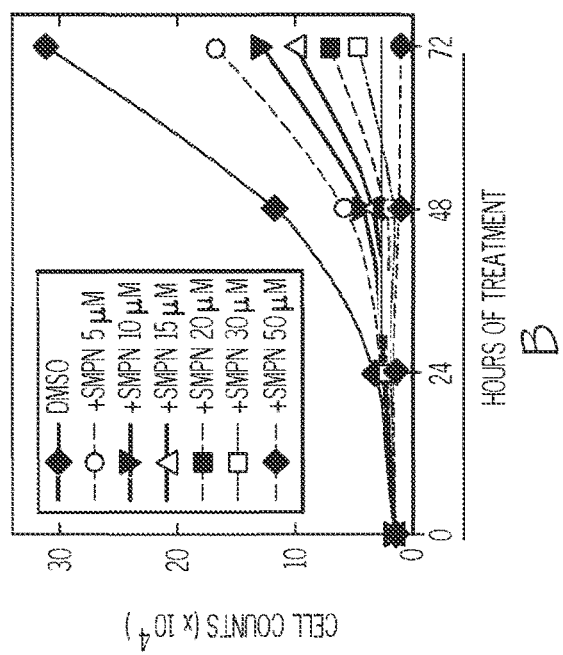
FIG. 2. 5MPN causes decreased proliferation of cancer cells preceded by a reduction in intracellular F2,6BP concentration, glycolysis and ATP.
Figure 2:
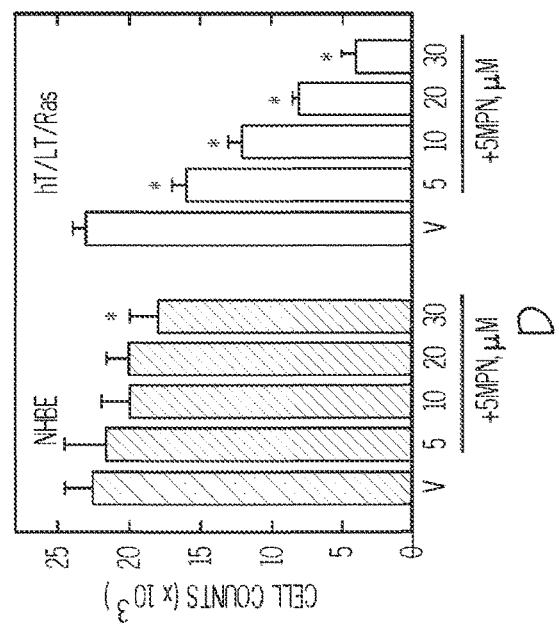
Figure 2:
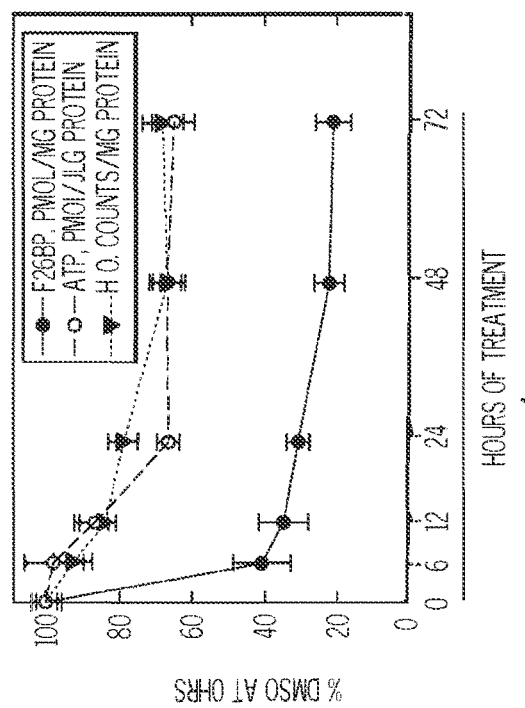
Figure 2:
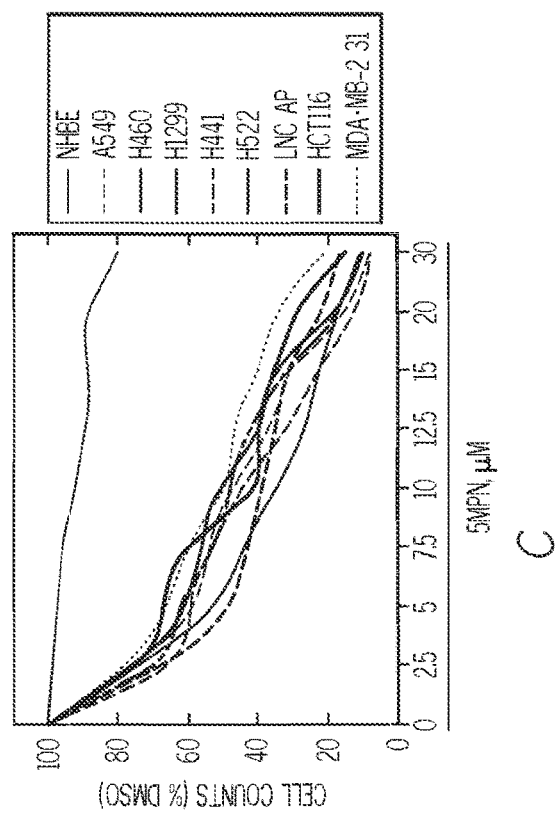
Figure 2:
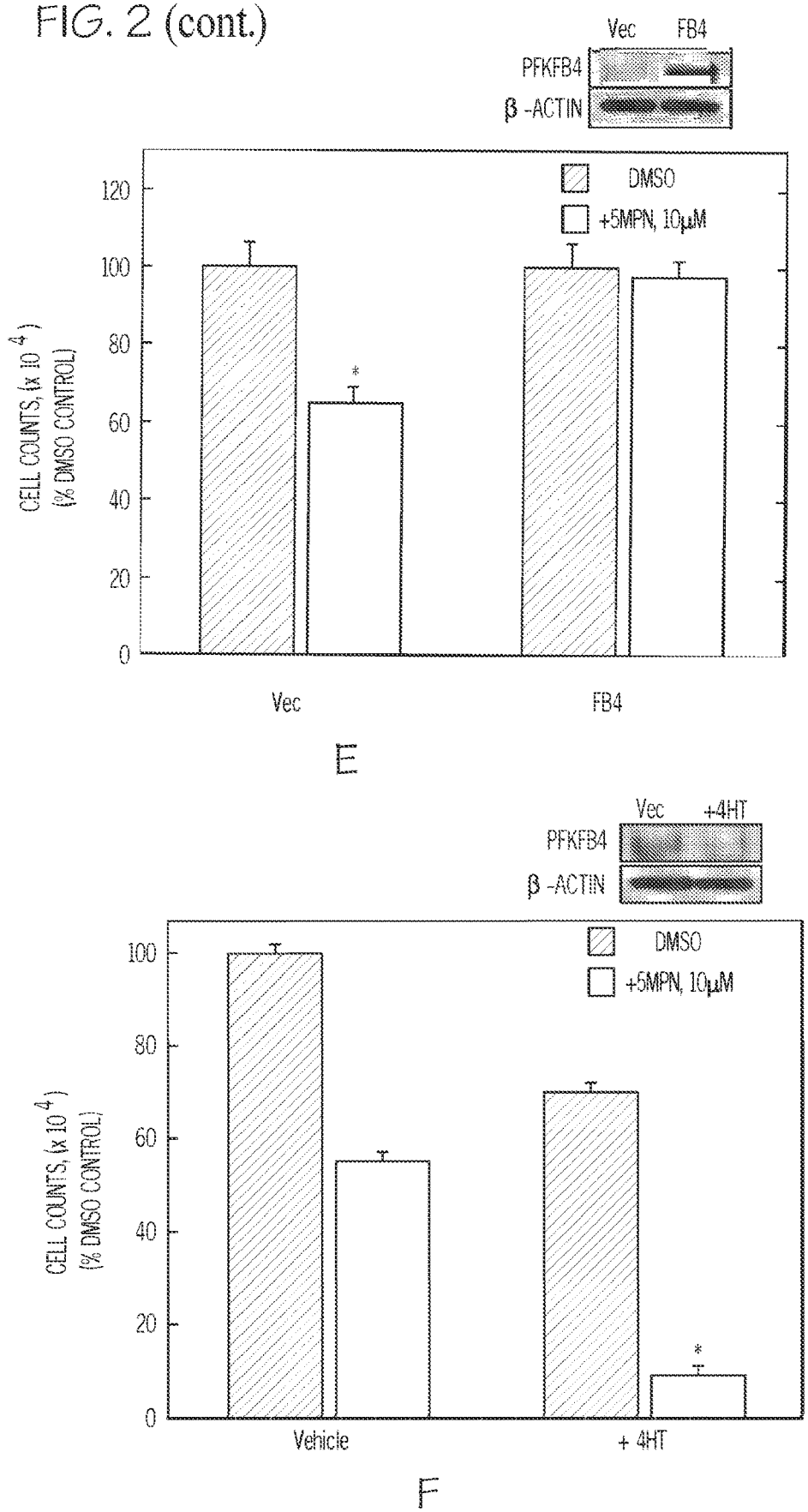

Pharmacological Inhibition of PFKFB4 by 5MPN is Selectively Cytostatic to Transformed Cells Results: H460 cells are lung adenocarcinoma cells that harbor several common oncogenic mutations (CDKN2A$^{del457}$, KRAS$^{Q61H}$, PIK3CA$^{E545K}$, STR11$^{Q37X}$) and are sensitive to inhibition of PFKFB4 using siRNA molecules. We examined the anti-metabolic effects of 5MPN on H460 cells and found that this agent reduced the intracellular concentration of F2,6BP, glycolysis and ATP (FIG. 2A) which in turn resulted in a reduction in cell proliferation (FIG. 2B). We also examined the effect of 5MPN on the proliferation of non-small cell lung cancer (H460, H1299, H441, H522 and A549), breast adenocarcinoma (MDA-MB-231), prostatic adenocarcinoma (LNCaP) and colon adenocarcinoma (HCT116) cell lines and observed a dose-dependent reduction in growth over 48 hours (FIG. 2C). Given that PFKFB4 has been found to be expressed by normal lung epithelia, we next examined the relative effects of 5MPN on normal human bronchial epithelial (NHBE) cells versus NHBE cells that had been sequentially immortalized with telomerase and large T antigen and transformed with H-Ras$^{V12}$ (hT/LT/Ras cells). We found that the NHBE cells were virtually unaffected whereas hT/LT/Ras cell growth was suppressed similar to other transformed cells (FIG. 2D). In order to interrogate the requirement of PFKFB4 inhibition for the observed suppression of proliferation (on-target effects), we next examined the effects of genetic modulation of PFKFB4 on the anti-proliferative effects of 5MPN. We found that whereas over-expression of PFKFB4 protected H460 cells from 5MPN, genomic deletion of Pfkfb4 sensitized cells to 5MPN (FIG. 2E and FIG. 2F), thus supporting the concept that inhibition of PFKFB4 by 5MPN is causing the observed reduction in H460 cell proliferation. Taken together, these data indicate that 5MPN is a potent inhibitor of PFKFB4 that selectively suppresses the proliferation of transformed cells.

Example 4

Figure 3:
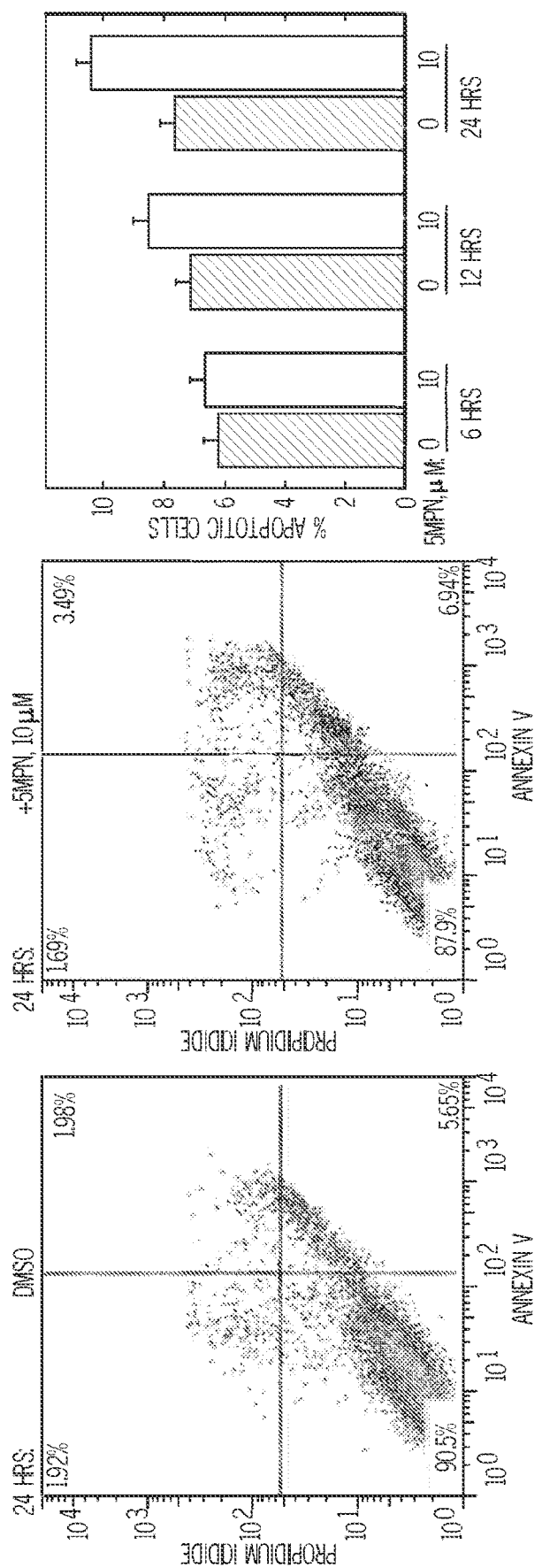
FIG. 3. 5MPN induces cell cycle arrest at the G1 phase.
Figure 3:
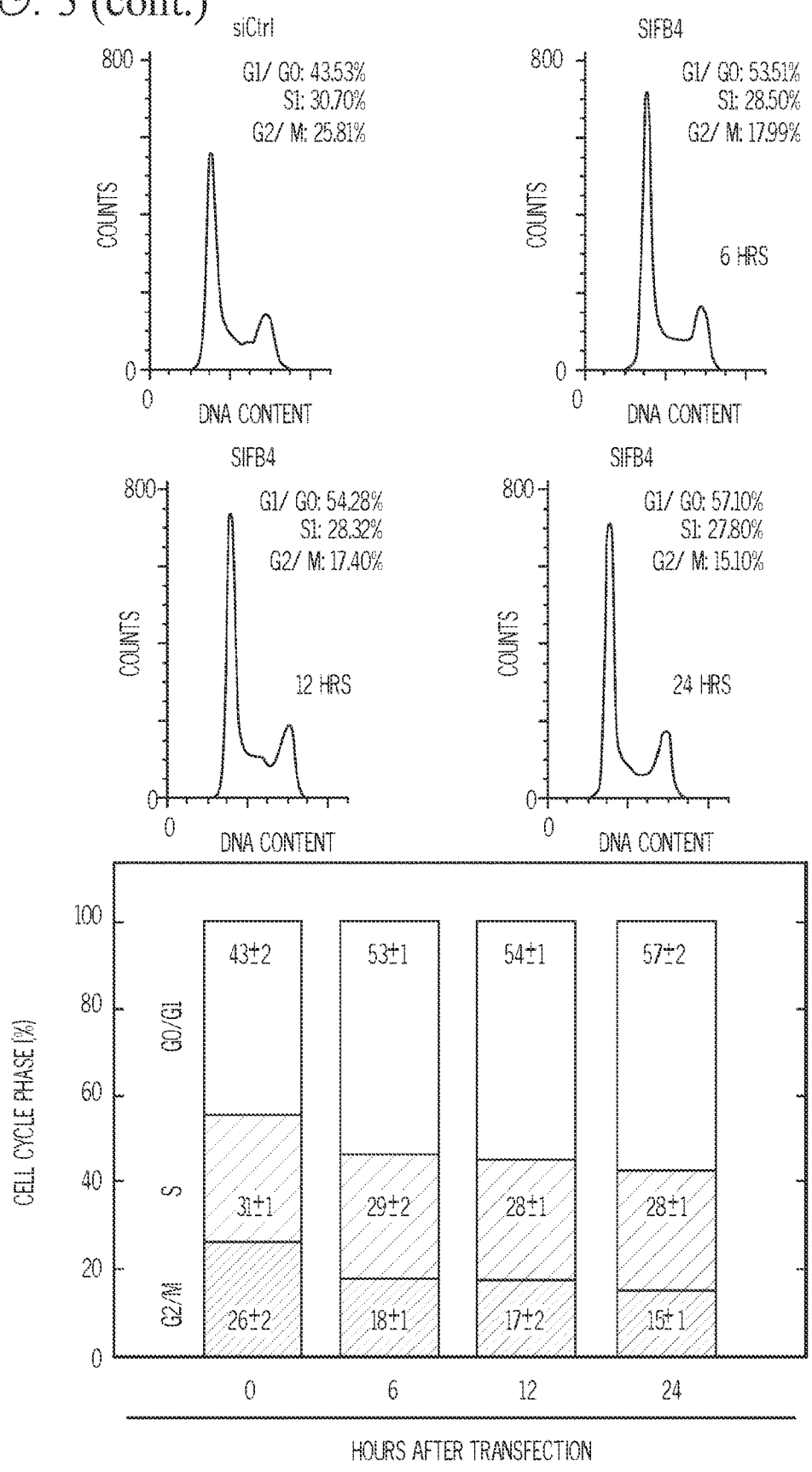
Figure 3:
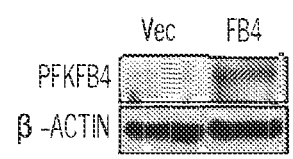
Figure 3:
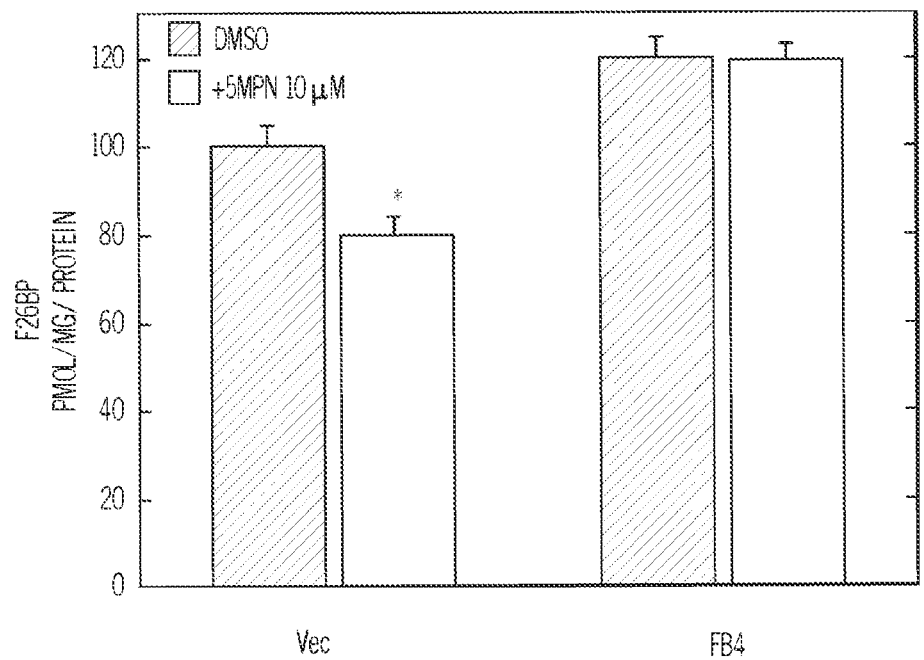
Figure 3:
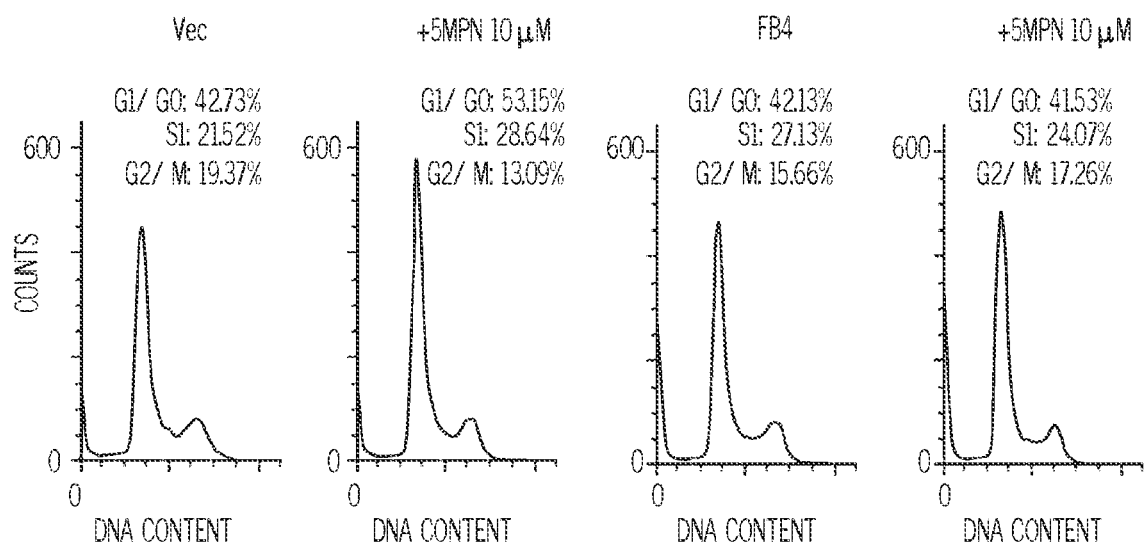

PFKFB4 Inhibition with 5PMN Causes a G1 Cell Cycle Arrest that is Reversed by PFKFB4 Over-Expression Results: We noted a marked reduction in viable H460 cells after exposure to 5MPN for 48 hours (see FIG. 2B) and postulated that 5MPN was inducing apoptosis, arresting cell cycle progression, or both. Whereas we observed only a minimal increase in apoptotic cells after 5MPN exposure or selective PFKFB4 siRNA transfection (FIG. 3A and FIG. 3B), we observed a marked G1 arrest with both 5MPN and PFKFB4 siRNA (FIG. 3C and FIG. 3D). We then over-expressed PFKFB4 and exposed the H460 cells to 5MPN at the indicated concentrations and assessed the effects on cell cycle and F2,6BP. We found that over-expression of PFKFB4 reversed the reduction in F2,6BP (FIG. 3E) and G1 arrest (FIG. 3F) caused by 5MPN. These studies suggest that 5MPN is suppressing PFKFB4 which in turn is resulting in a reduction in the G1/S transition.

Example 5

Figure 4:
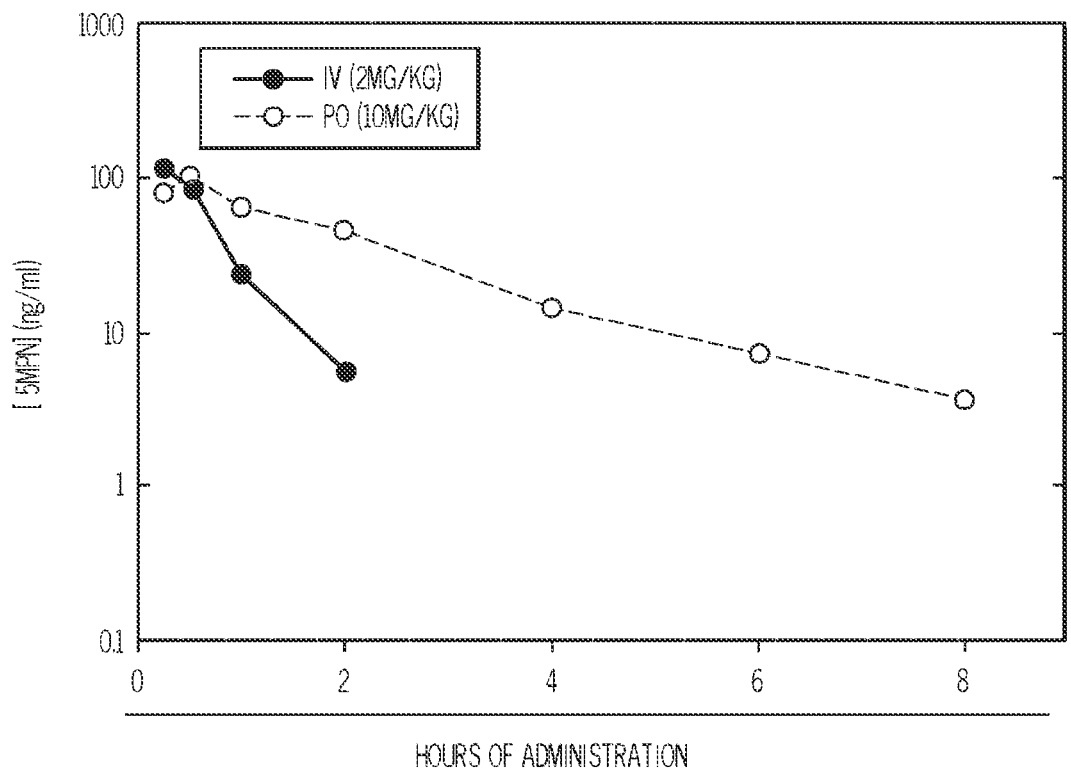
FIG. 4. 5MPN has high oral bioavailability and suppresses glucose uptake and tumor growth in mice.
Figure 4:
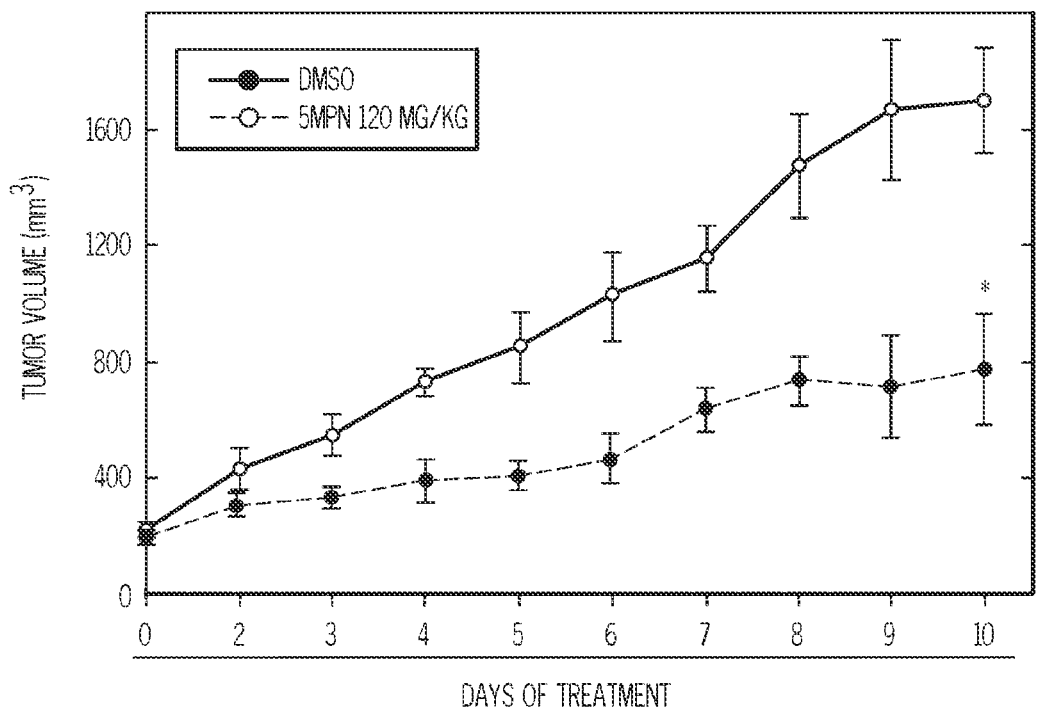
Figure 4:
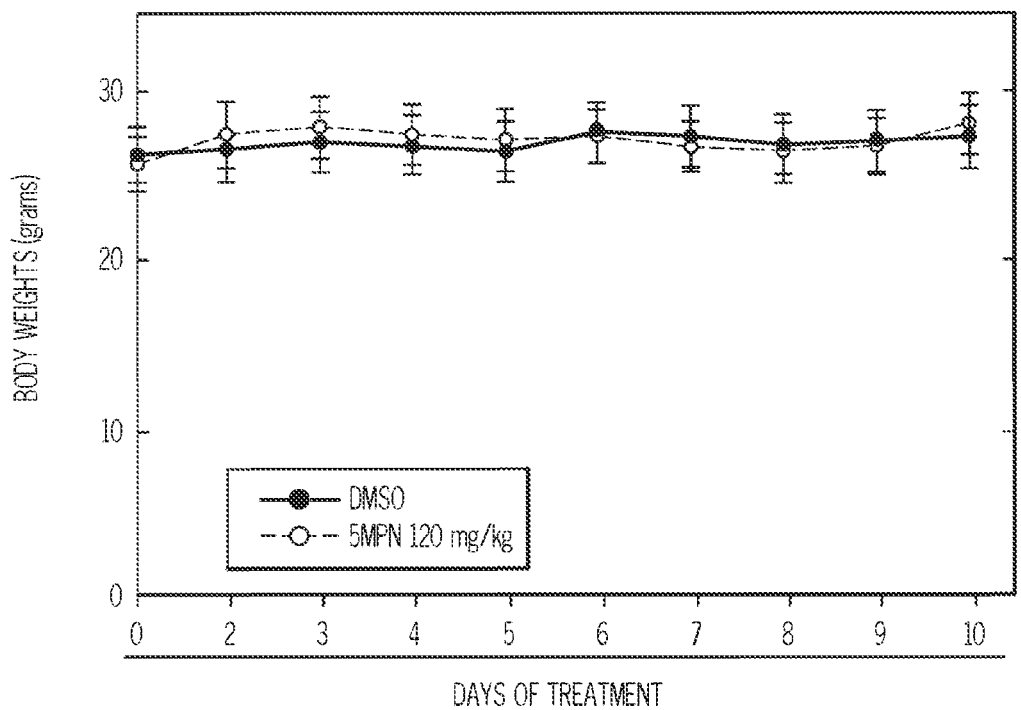
Figure 4:
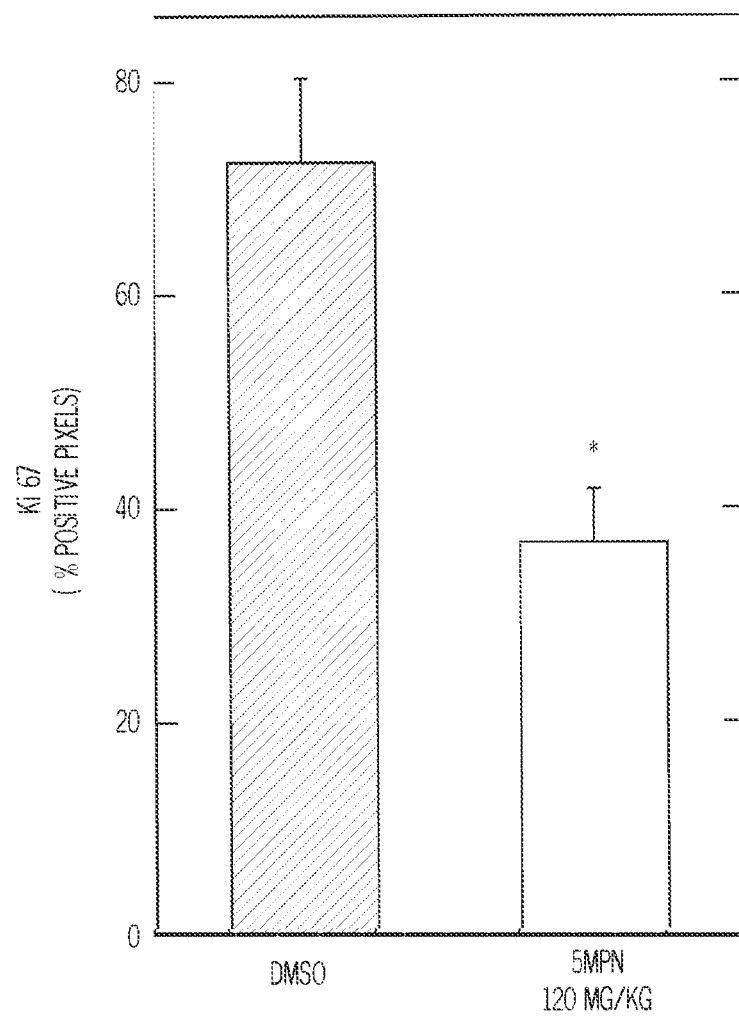
Figure 4:
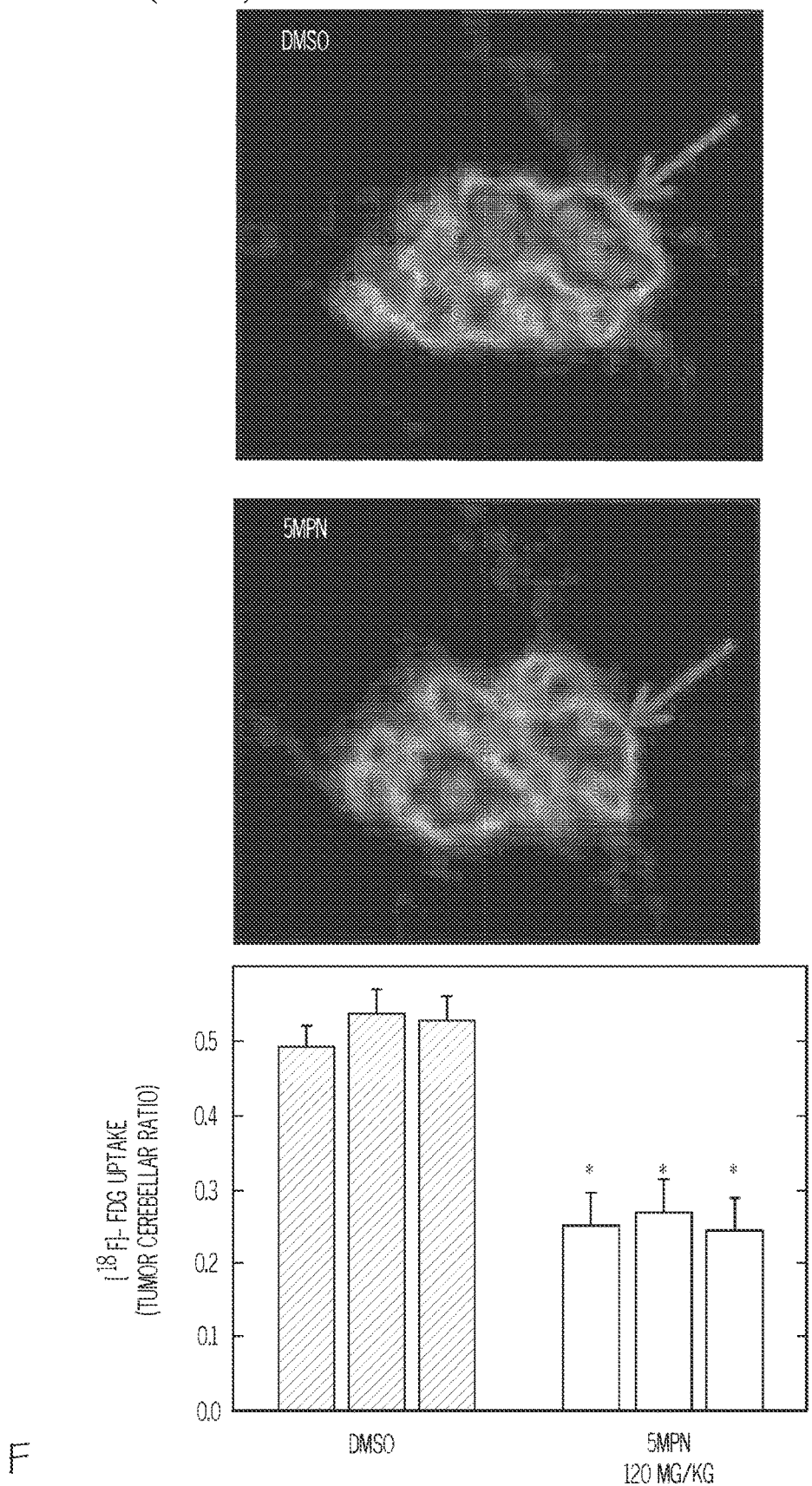
Figure 4:
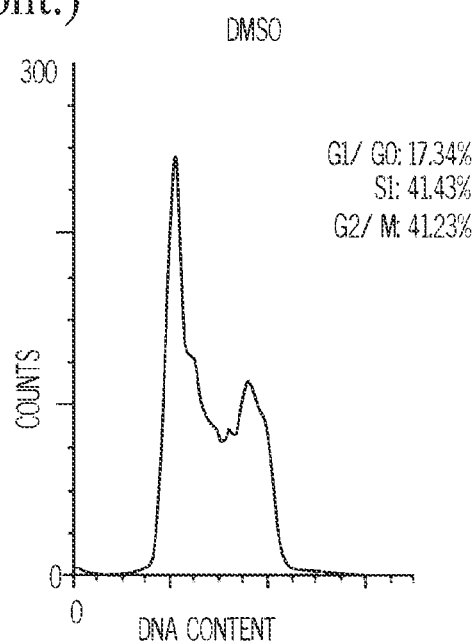
Figure 4:
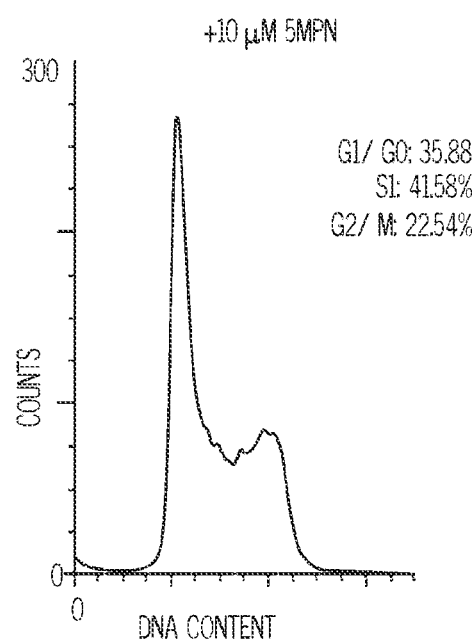
Figure 4:
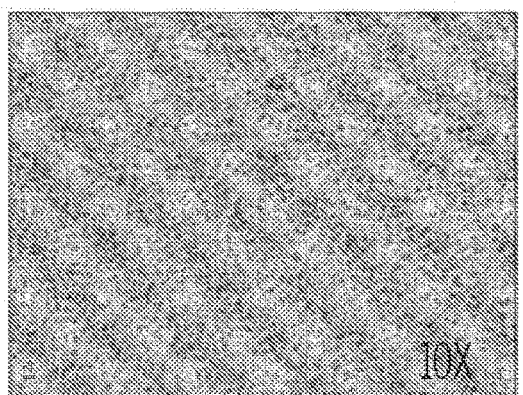
Figure 4:
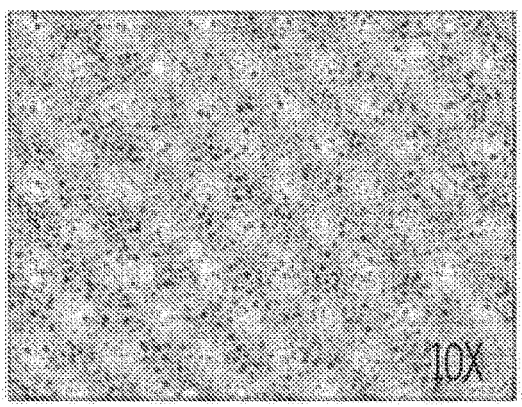
Figure 4:
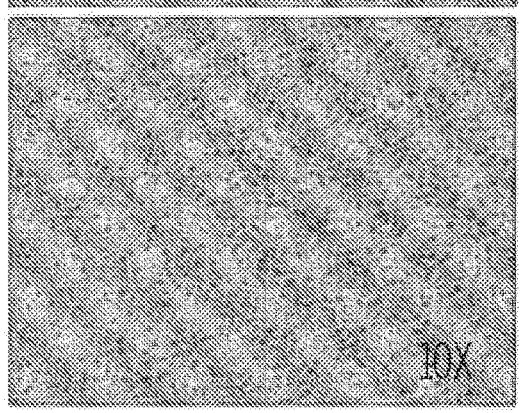
Figure 4:
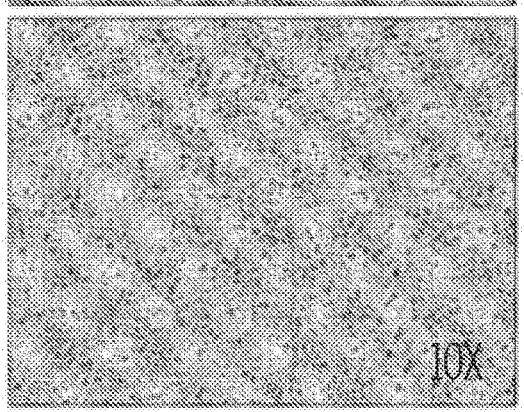
Figure 4:
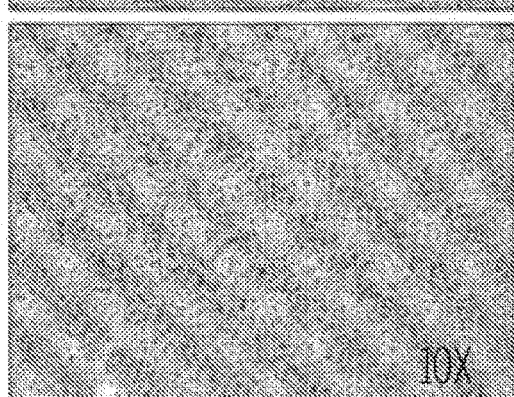
Figure 4:
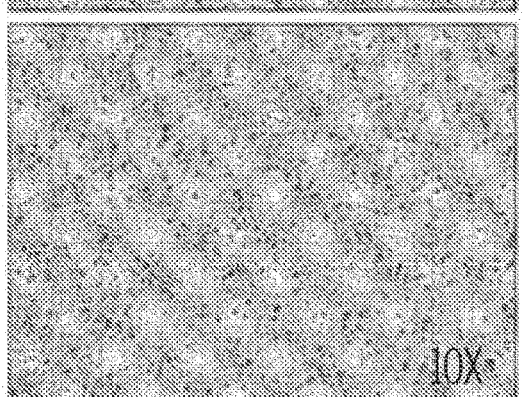
Figure 4:
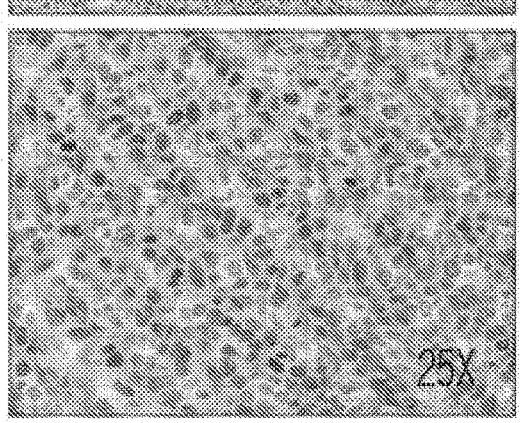
Figure 4:
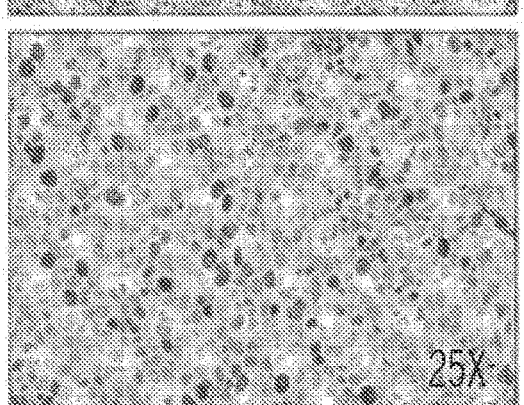
Figure 4:
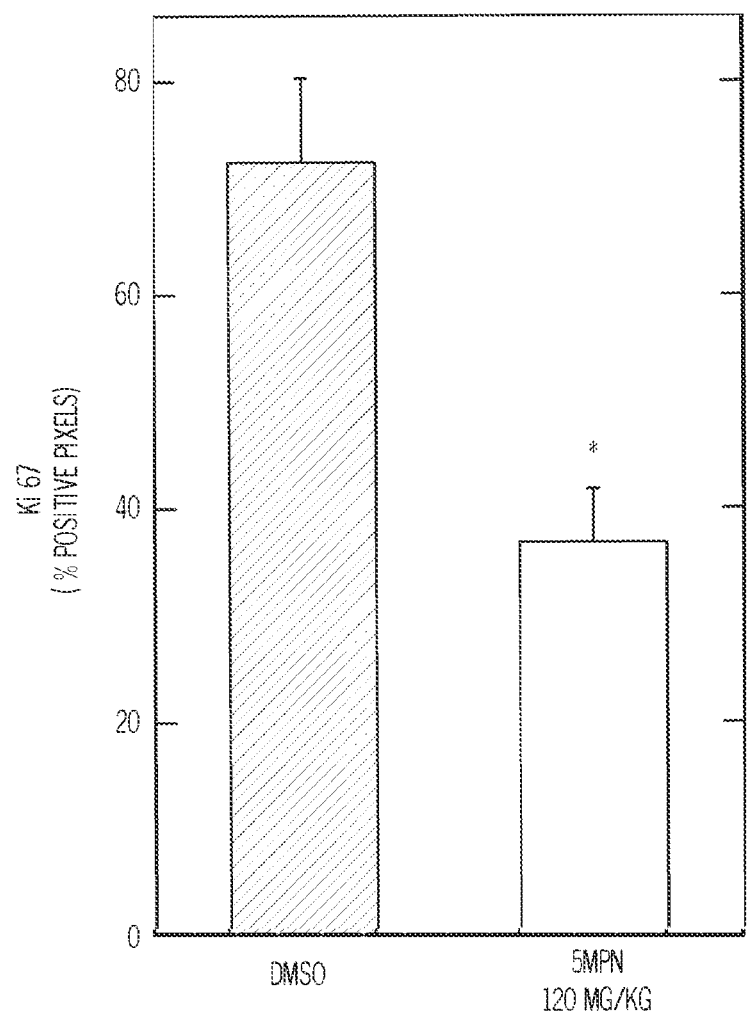
Figure 4:
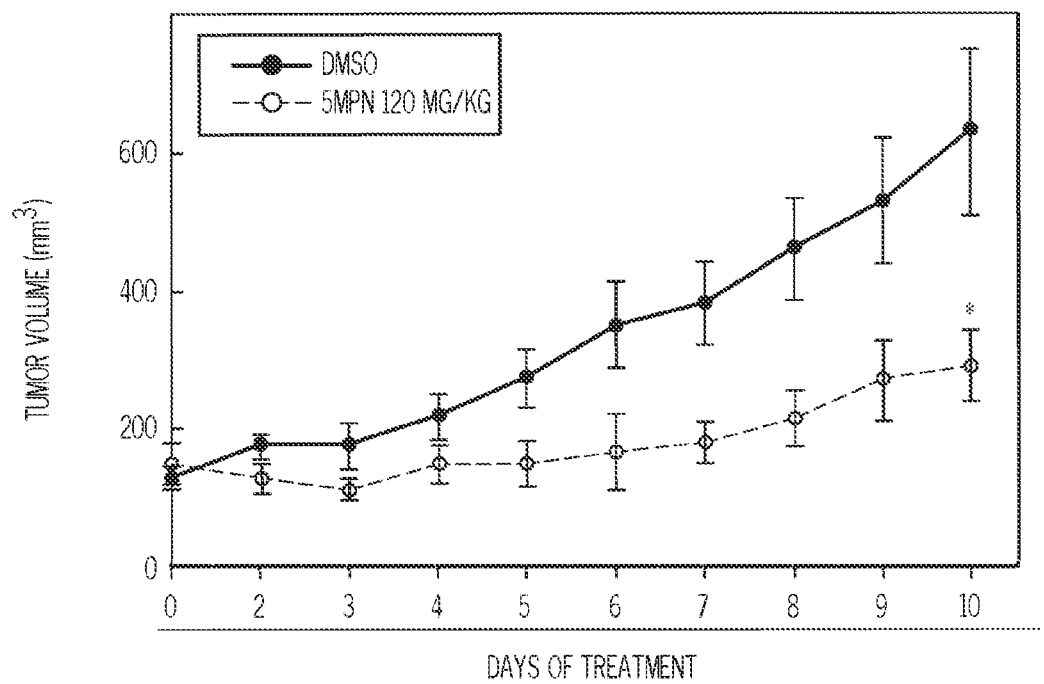
Figure 4:
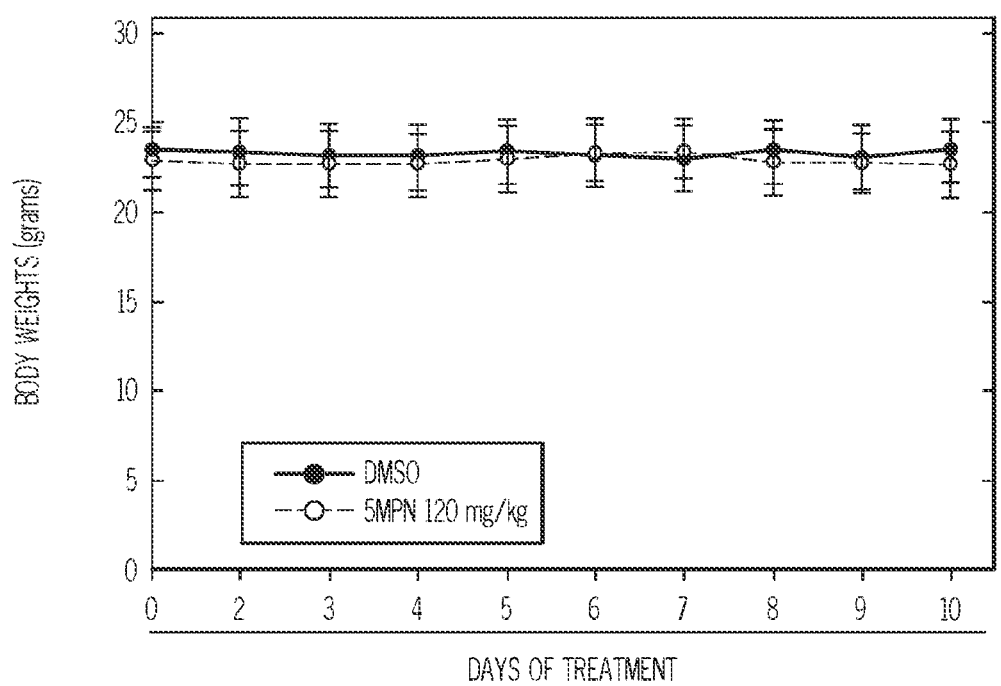

5MPN has High Oral Bioavailability and Suppresses the Glucose Uptake and Growth of Tumors in Mice Results: The pharmacokinetics of intravenous and oral administration of 5MPN was studied and revealed that both routes were adequate to achieve potentially therapeutic concentrations when administered daily (FIG. 4A and FIG. 4B). Given the potential usefulness of oral administration in terms of cost and convenience, we elected to pursue this route in subsequent toxicity and efficacy pre-clinical studies. Initially, we dosed C57BL/6 mice with 120 mg/kg PO for two weeks and analyzed the effect on complete blood counts, electrolytes, hepatic and renal function, body mass and the gross and histological appearance of the brain, heart, lungs, liver, kidneys and spleen. We found no signs of toxicity either from these objective measures or from any behavioral or clinical changes (i.e. ruffled fur, lethargy, ataxia or labored respiration). Importantly, at this oral dose, it was determine that 5MPN suppressed the growth of Lewis lung carcinomas grown in syngeneic mice (FIG. 4C) and H460 human lung adenocarcinoma xenografts grown in athymic mice (FIG. 4J) without affecting body weight (FIG. 4D and FIG. 4K). Next, the effects of oral administration of 5MPN on intratumoral F2,6BP and glucose uptake by LLC xenografts was examined. There was a marked reduction in F2,6BP (FIG. 4E) and 2-[$^{18}$F]-fluoro-2-deoxyglucose uptake using positron emission tomography (FIG. 4F). It was confirmed that 5MPN caused a G1 arrest in LLC cells in vitro similar to H460 cells (FIG. 4G). The number of Ki67-positive cells was examined since Ki-67 expression correlates with later S and G2 phases of the cell cycle (Sasaki K et al. The cell cycle associated change of the Ki-67 reactive nuclear antigen expression. J Cell Physiol 1987 December; 133(3):579-84). It was determined that oral administration of 5MPN caused a reduction in Ki67-positive cells in the LLC xenografts (FIG. 4H and FIG. 4I) suggesting that 5MPN may be reducing cell cycle progression in vivo.

Example 6

Figure 5:
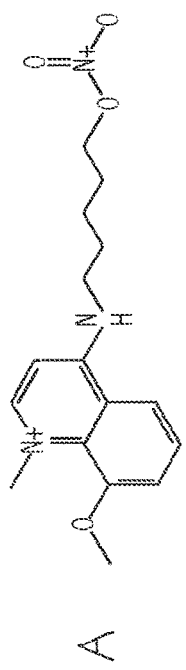
FIG. 5. MPN-2 inhibits recombinant PFKFB4 enzyme activity, decreases the production of F2,6BP, decreased proliferation of cancer cells, and has high oral bioavailability.
Figure 5:
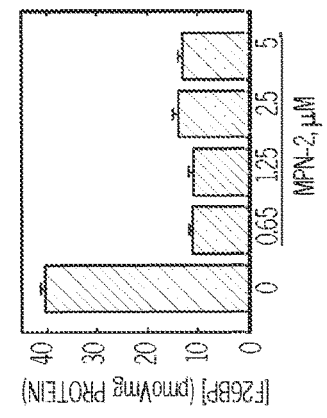
Figure 5:
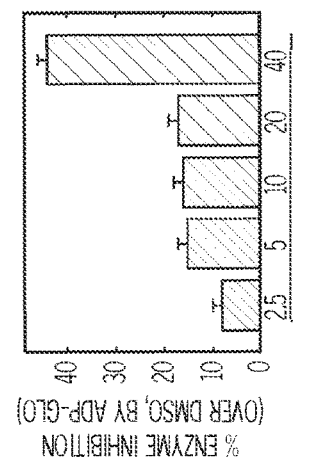
Figure 5:
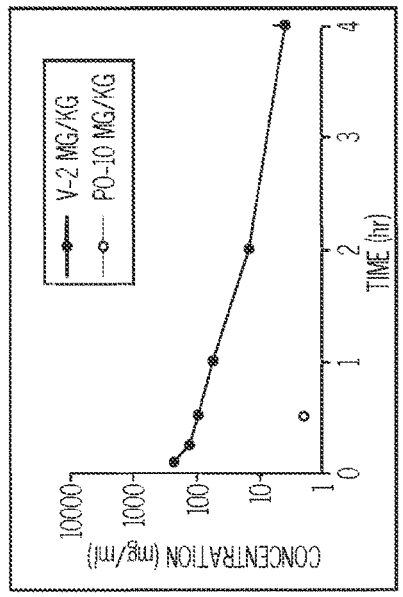
Figure 5:
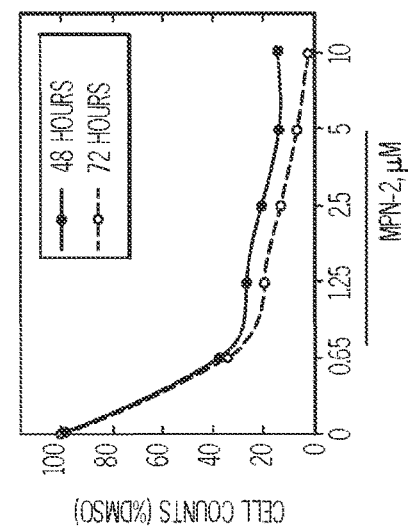

MPN-2 Inhibits Recombinant PFKFB4 Enzyme Activity, Decreases the Production of F2,6BP, Decreased Proliferation of Cancer Cells, and has High Oral Bioavailability Results: 5-[(8-methoxy-2-methylquinolin-1-ium-4-yl) amino]pentyl nitrate (MPN-2) significantly inhibited PFKFB4 activity (FIG. 5B) and F2,6BP production (FIG. 5C). MPN-2 decreased the proliferation of a human cancer cell line, H460 NSCLC (FIG. 5D). Viable cells counted at 48 hours and at 72 hours. Pharmacokinetic analysis of intravenous and oral administration of MPN-2 determined that MPN-2 exhibits high oral bioavailability. FIG. 5E shows the oral and intravenous pharmacokinetic properties of MPN-2 in CD-1 mice (N=3)

Example 7

Figure 6:
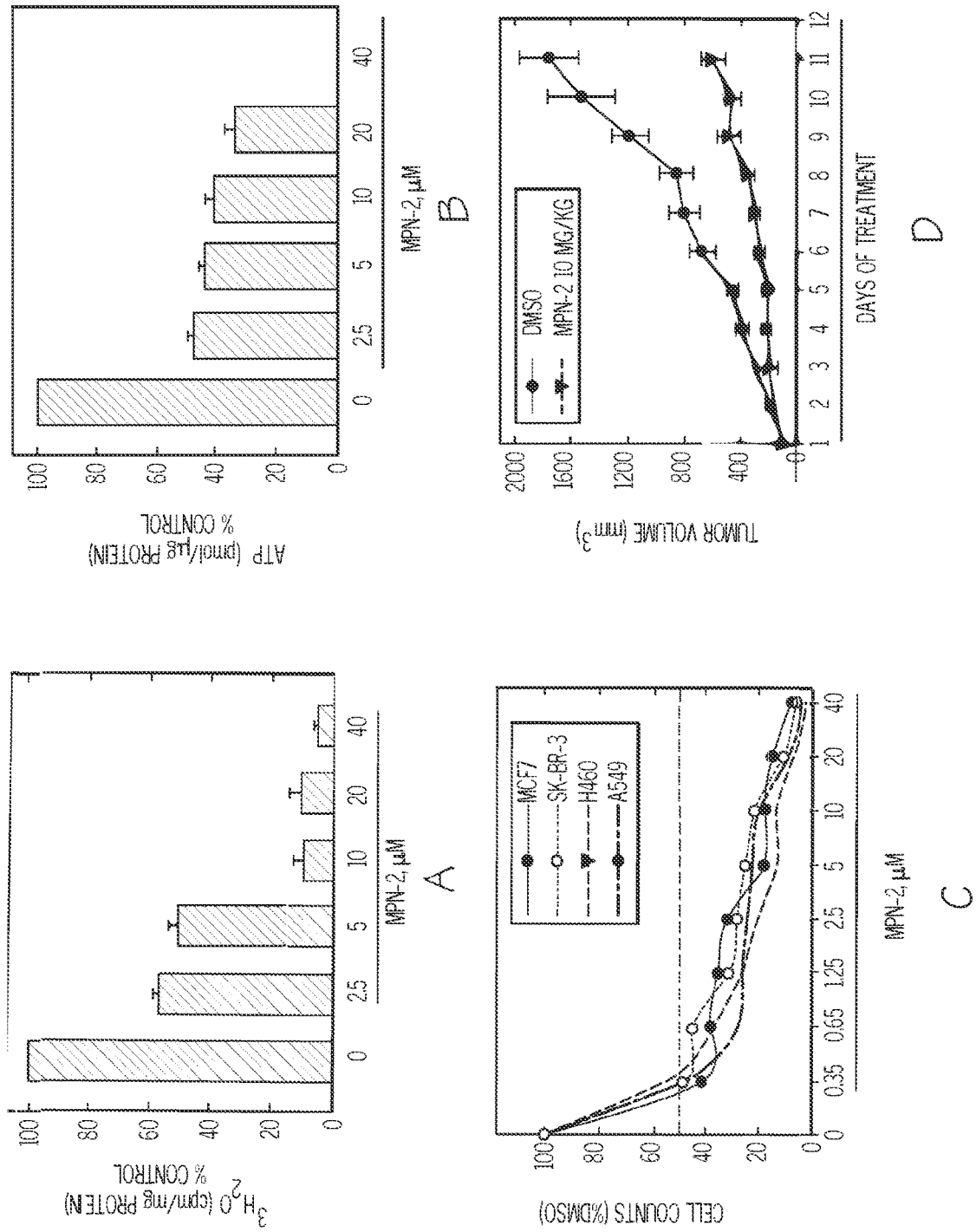
FIG. 6. MPN-2 causes decreased proliferation of cancer cells preceded by a reduction in intracellular glycolysis and ATP, decreased proliferation of cancer cells, and tumor growth in mice.

MPN-2 Causes Decreased Proliferation of Cancer Cells Preceded by a Reduction in Intracellular Glycolysis and ATP, Decreased Proliferation of Cancer Cells, and Tumor Growth in Mice Results: MPN-2 significantly decreased intracellular glycolysis (FIG. 6A) and ATP (FIG. 6B) production of H460 NSCLC cells treated with DMSO±the indicated concentrations of MPN-2. The effects on glycolysis (FIG. 6A) and ATP (FIG. 6B) were measured after 48 hours. Furthermore, MPN-2 significantly decreased the proliferation of various cancer cell lines. FIG. 6C shows the decreased proliferation of MCF7, SK-BR-3, H460, and A549 cells exposed to DMSO±the indicated concentrations of MPN-2 after 24-72 hours (72 hours shown). Furthermore, it was determined that MPN-2 suppressed the growth of Lewis lung carcinomas grown in C57BL/6 mice (FIG. 6D). When tumors reached a mass of 150-200 mg, mice were randomized to daily administration of DMSO or 5MPN in DMSO at the indicated dose by intraperitoneal injection (10 mg/kg, for eleven days).

Example 8

Formula IV Compounds Decreased Proliferation of Cancer Cells

Results: We also examined the effect of the compounds of Formula IV on the proliferation of H460 non-small cell lung cancer, H460. Formula IV compounds, specifically

Figure 7:
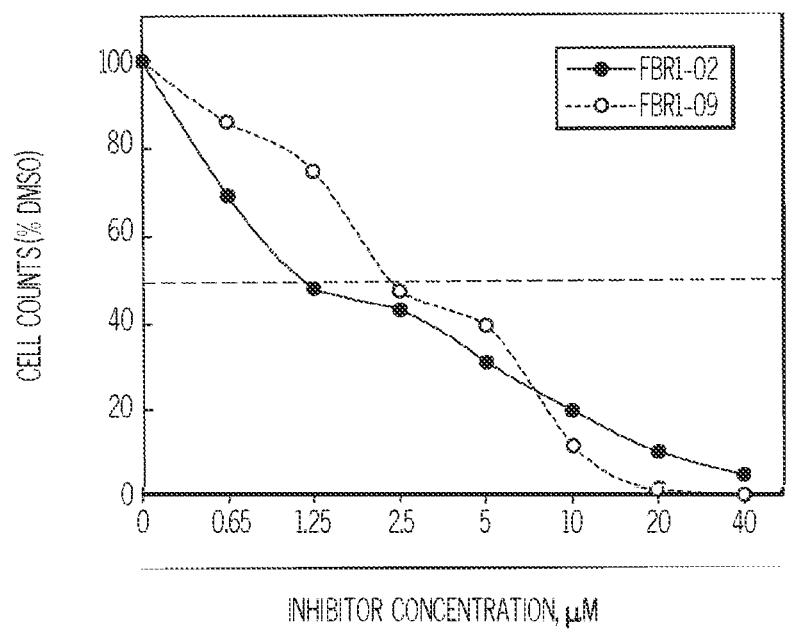
FIG. 7. Formula IV compounds decreased proliferation of cancer cells.

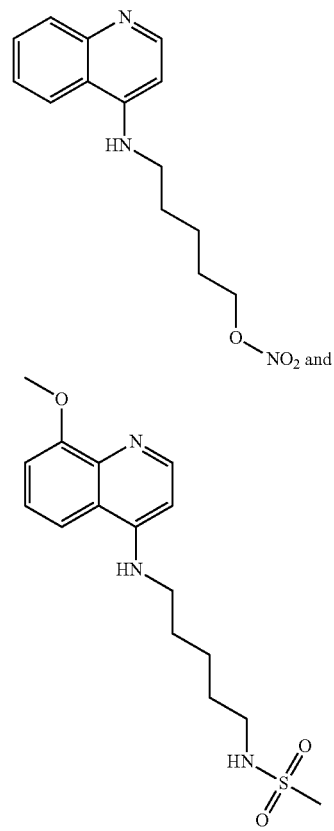

significantly decreased the proliferation of the H460 NSCLC cells (FIG. 7).

Example 9

Dual PFKFB4 and PFKFB3 Inhibition with MPN-2 and PFK15, Respectively, Causes a Synergistic Increase in Cell Death Results: Studies conducted by the instant investigators have revealed that PFKFB4 expression is increased by PFKFB3 inhibition, suggesting that PFKFB4 may compensate for decreased PFKFB3 expression and activity and, importantly, may limit the efficacy of PFKFB3 inhibitors, including PFK15 (Tocris). Thus, we also examined the effect of combination therapy of a PFKFB4 inhibitor and a PKFB3 inhibitor. FIG. 8 shows that simultaneous administration of MPN-2 (determined by the instant investigators to be a PFKFB4 inhibitor) and PFK15 (Tocris, a commercially available PFKFB3 inhibitor) synergistically increased cell death in vitro. Thus, combination therapy with PFK15 (and other PFKFB3 inhibitors) and the presently-disclosed small molecule antagonists of the kinase domain of PFKFB4 may be used to provide an effective chemotherapeutic regimen.

Example 10

Synthesis of the Small Molecule Antagonists of the Kinase Domain of PFKFB4 (Including Various Compounds of Formulae (I), (II), and (III), (IV), (V), (VI), and (VII))

Referring to FIG. 9, the synthesis of the instantly disclosed small molecule antagonists of the kinase domain of PFKFB4 (including various compounds of Formulae (I), (II), and (III), (VI), (V), (VI), and (VII) began with the condensation of Meldrum's acid (1) with aniline 2 in the presence of trimethyl orthoformate to afford adduct 3 in excellent yield (Dutta, A. K.; et al. Discovery of 4-(4-(2-((5-Hydroxy-1,2,3,4-tetrahydronaphthalen-2-yl)(propyl)amino)ethyl)piperazin-1-yl)quinolin-8-ol and Its Analogues as Highly Potent Dopamine D2/D3 Agonists and as Iron Chelator: In Vivo Activity Indicates Potential Application in Symptomatic and Neuroprotective Therapy for Parkinson's Disease. *J. Med Chem.* 2010.53.2114-2125). Cyclization was facilitated by heating 3 in diphenyl ether to produce 8-methoxyquinolin-4-ol (4) core, which was subsequently converted to chloride 5 by refluxing in phosphoryl chloride (Id.). The carbon linker was installed by heating chloride 5 with a commercially available primary amine (Perez, B. C.; et al. N-Cinnamoylated Chloroquine Analogues as Dual-Stage Antimalarial Leads. *J. Med Chem.* 2013.56, 556-567). In the final step, several conditions were surveyed for nitric acid ester formation and many were sluggish or produced multiple byproducts. Ultimately, treating alcohol 6 with concentrated nitric acid, acetic acid, and acetic anhydride in ethyl acetate produced the desired product (Kourounakis, P. N. et al. Nitric oxide releasing derivatives of tolfenamic acid with anti-inflammatory activity and safe gastrointestinal profile. *Bioorg. Med Chem.* 2005, 13, 6485-6492.)

Still referring to FIG. 9, the synthesis is amendable to produce a library of derivatives. For example, the carbon linker can be altered by treating chloride 5 with a variety of nucleophiles. Furthermore, the primary alcohol of compound 6 can be functionalized with groups other than the nitric acid ester. Attempts were made to prepare the 2-methylquinoline salt by treating 7 with methyl iodide in acetonitrile. Decomposition was observed. Tt is hypothesized that the salt may need to be prepared prior to the installation of the nitric acid ester.

All documents cited are incorporated herein by reference; the citation of any document is not to be construed as an admission that it is prior art with respect to the present invention

The invention claimed is:

1. A pharmaceutical composition comprising a compound of Formula (IV)

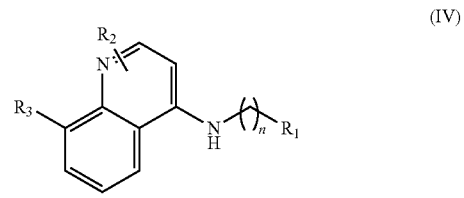

(IV)

wherein:

n is 4-6;

$R_1$ is carboxylic acid (—CO—OH), methyl sulfonamide (—NH—SO$_2$—CH$_3$), carboxylic acid methyl ester (—CO—OCH$_3$), or tert-butyl carbamate (—NH—CO—OC(CH$_3$)$_3$);

$R_2$ is hydrogen or $C_2$-$C_5$ alkyl;

$R_3$ is $C_1$-$C_5$ alkoxy; and wherein if $R_2$ is $C_2$-$C_5$ alkyl and located on the nitrogen of the quinoline group, then the nitrogen has a positive charge; and wherein when $R_1$ is carboxylic acid or carboxylic acid methyl ester, then $R_2$ is hydrogen;

and at least one pharmaceutical excipient.

2. The pharmaceutical composition of claim 1, wherein the compound is present in an amount that specifically inhibits PFKFB4.

3. The pharmaceutical composition of claim 1, wherein the pharmaceutical composition is formulated for oral administration or is formulated for intravenous administration.

4. The pharmaceutical composition of claim 1, wherein n=5, $R_1$ is methyl sulfonamide, or $R_3$ is methoxy, or a combination thereof.

5. The pharmaceutical composition of claim 1, wherein $R_1$ is methyl sulfonamide.

6. The pharmaceutical composition of claim 1, wherein the compound is selected from the group consisting of:

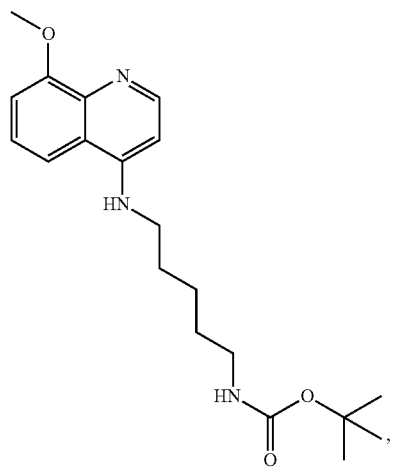

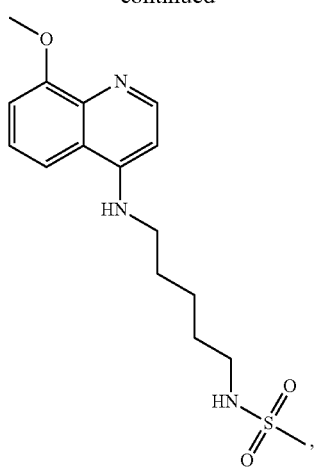
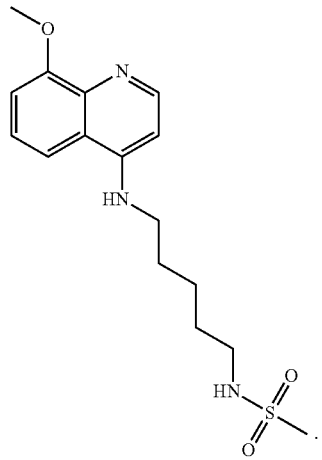 [SMILES: COc1cccc2c(NCCCCCNS(C)(=O)=O)ccnc12]
8. The pharmaceutical composition of claim 1, wherein the compound is
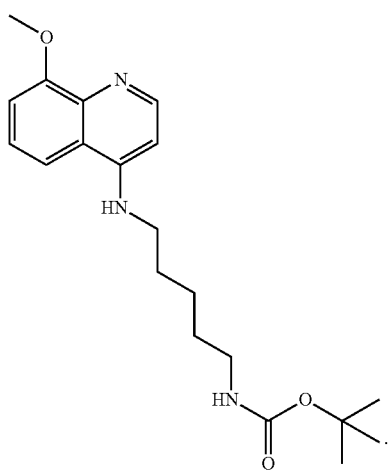 [SMILES: COc1cccc2c(NCCCCCNC(=O)OC(C)(C)C)ccnc12]
9. The pharmaceutical composition of claim 1, wherein the compound is
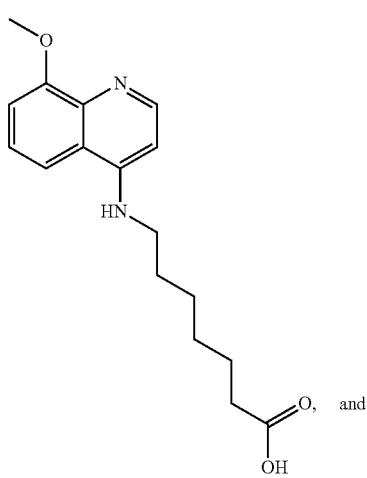
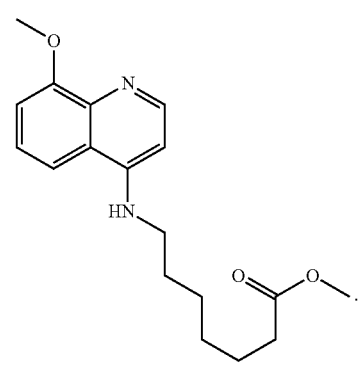
7. The pharmaceutical composition of claim 1, wherein the compound is
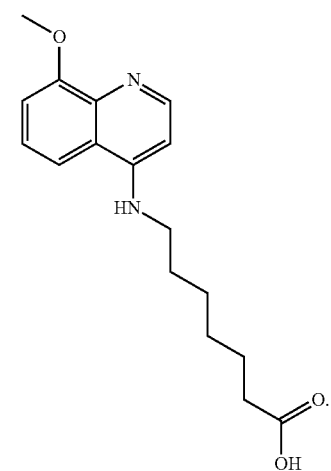 [SMILES: COc1cccc2c(NCCCCCCC(=O)O)ccnc12]
10. The pharmaceutical composition of claim 1, wherein the compound is

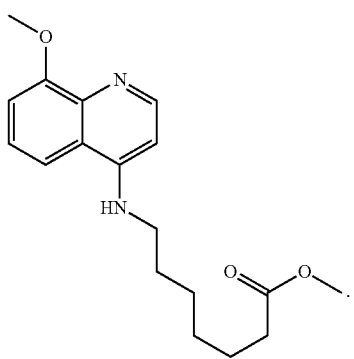

11. The pharmaceutical composition of claim 1, wherein $R_2$ is hydrogen.

12. A method of inhibiting PFKFB4 in a subject in need thereof, the method comprising administering to the subject an effective amount of a compound of Formula (IV):

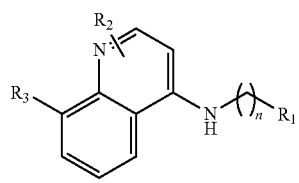

(IV)

wherein:

n is 4-6;

$R_1$ is carboxylic acid (—CO—OH), methyl sulfonamide (—NH—SO$_2$—CH$_3$), carboxylic acid methyl ester (—CO—OCH$_3$), or tert-butyl carbamate (—NH—CO—OC(CH$_3$)$_3$);

$R_2$ is hydrogen or C$_2$-C$_5$ alkyl;

$R_3$ is C$_1$-C$_5$ alkoxy; and wherein if $R_2$ is C$_2$-C$_5$ alkyl and located on the nitrogen of the quinoline group, then the nitrogen has a positive charge; and wherein when $R_1$ is carboxylic acid or carboxylic acid methyl ester, then $R_2$ is hydrogen.

13. The method of claim 12, wherein the compound of Formula (IV) is administered at a dosage effective for specifically inhibiting PFKFB4.

14. The method of claim 12, wherein the compound of Formula (IV) is administered orally or intravenously.

15. The method of claim 12, wherein the subject remains substantially free of signs of toxicity.

16. The method of claim 12, wherein n=5, $R_1$ is methyl sulfonamide, or $R_3$ is methoxy, or a combination thereof.

17. The method of claim 12, wherein n=5, $R_1$ is methyl sulfonamide, and $R_3$ is methoxy.

18. The method of claim 12, wherein the compound is

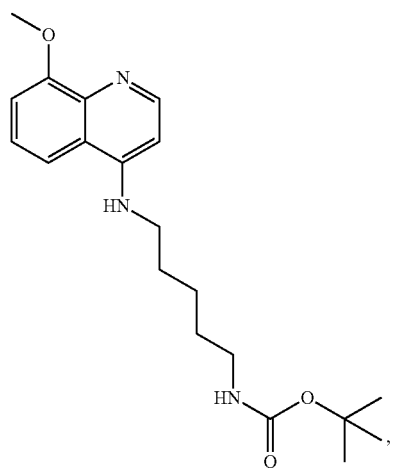

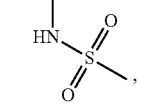

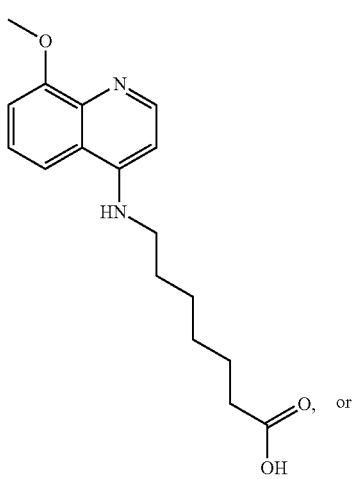

, or

-continued
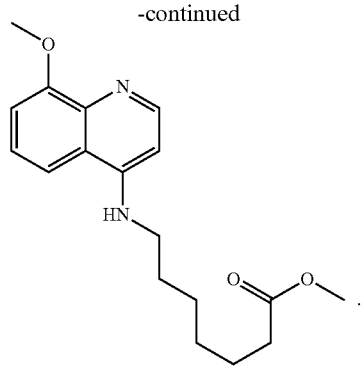
19. The method of claim 12, wherein $R_2$ is hydrogen.
* * * * *